ary Examiner—Janet L. Andres

(12) United States Patent
Finke et al.

(10) Patent No.: US 7,572,785 B2
(45) Date of Patent: Aug. 11, 2009

(54) SUBSTITUTED IMIDAZOLES AS CANNABINOID RECEPTOR MODULATORS

(75) Inventors: Paul E. Finke, Milltown, NJ (US); Sander G. Mills, Scotch Plains, NJ (US); Christopher W. Plummer, Keasbey, NJ (US); Shrenik K. Shah, Metuchen, NJ (US); Quang T. Truong, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 304 days.

(21) Appl. No.: 11/265,850

(22) Filed: Nov. 3, 2005

(65) Prior Publication Data

US 2006/0089356 A1  Apr. 27, 2006

Related U.S. Application Data

(62) Division of application No. 10/198,442, filed on Jul. 17, 2002, now Pat. No. 7,057,051.

(60) Provisional application No. 60/307,224, filed on Jul. 20, 2001.

(51) Int. Cl.
*A61K 31/55* (2006.01)
*C07D 405/00* (2006.01)
*C07D 413/00* (2006.01)

(52) U.S. Cl. .................. 514/217.09; 514/235.18; 514/326; 544/141; 546/210

(58) Field of Classification Search ............... 546/210; 544/141; 514/217.09, 235.18, 326
See application file for complete search history.

(56) References Cited

U.S. PATENT DOCUMENTS

| | | | |
|---|---|---|---|
| 4,820,757 A | 4/1989 | Spang et al. | |
| 4,973,587 A | 11/1990 | Ward et al. | |
| 5,013,837 A | 5/1991 | Ward et al. | |
| 5,081,122 A | 1/1992 | Ward | |
| 5,112,820 A | 5/1992 | Ward | |
| 5,260,322 A | 11/1993 | Nakasimi et al. | |
| 5,292,736 A | 3/1994 | Kumar et al. | |
| 5,462,960 A | 10/1995 | Barth et al. | |
| 5,532,237 A | 7/1996 | Gallant et al. | |
| 5,624,941 A | 4/1997 | Barth et al. | |
| 5,840,721 A | 11/1998 | Mjalli et al. | |
| 5,925,768 A | 7/1999 | Barth et al. | |
| 6,028,084 A | 2/2000 | Barth et al. | |
| 6,344,474 B1 | 2/2002 | Maruani et al. | |
| 7,057,051 B2 * | 6/2006 | Finke et al. ............ 548/334.5 |
| 2005/0026983 A1 | 2/2005 | Carpino | |
| 2005/0065189 A1 | 3/2005 | Lange et al. | |

FOREIGN PATENT DOCUMENTS

| | | |
|---|---|---|
| EP | 0 353 606 | 2/1990 |
| EP | 0 284 828 | 10/1991 |
| EP | 0 658 546 | 12/1994 |
| EP | 0 701 819 | 3/1996 |
| EP | 0 576 357 | 3/1997 |
| EP | 0 656 354 | 6/1997 |
| EP | 0 876 350 | 7/2001 |
| JP | 63-010767 | 1/1988 |
| JP | 63-107963 | 5/1988 |
| JP | 8-41324 | 2/1996 |
| JP | 9-169737 | 6/1997 |
| WO | WO 92/05148 | 4/1992 |
| WO | WO 93/19045 | 9/1993 |
| WO | WO 97/29079 | 8/1997 |
| WO | WO 98/27108 | 6/1998 |
| WO | WO 98/31227 | 7/1998 |
| WO | WO 98/37061 | 8/1998 |
| WO | WO 98/41519 | 9/1998 |
| WO | WO 98/43635 | 10/1998 |
| WO | WO 98/43636 | 10/1998 |

(Continued)

OTHER PUBLICATIONS

Little et al., J. of Pharm. & Exp. Therap., vol. 247 (1988), pp. 1046-1051, "Pharmacology and stereoselectivity of structurally novel cannabinoids in mice".

Kuster et al., J. of Pharm. & Exp. Therap., vol. 264 (1993), pp. 1352-1363, "Aminoalkylindole binding in rat cerebellum: Selective displacement by natural and synthetic cannabinoids".

Rinaldi-Carmona et al., FEBS Letters, vol. 350 (1994), pp. 240-244, "SR141716A, a potent and selective antagonist of the brain cannabinoid receptor".

(Continued)

*Primary Examiner*—Janet L. Andres
*Assistant Examiner*—Raymond Covington
(74) *Attorney, Agent, or Firm*—Baerbel R. Brown; Catherine D. Fitch

(57) ABSTRACT

The use of compounds of the present invention as antagonists and/or inverse agonists of the Cannabinoid-1 (CB1) receptor particularly in the treatment, prevention and suppression of diseases mediated by the Cannabinoid-1 (CB1) receptor. The invention is concerned with the use of these novel compounds to selectively antagonize the Cannabinoid-1 (CB1) receptor. As such, compounds of the present invention are useful as psychotropic drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, and schizophrenia. The compounds are also useful for the treatment of substance abuse disorders, particularly to opiates, alcohol, and nicotine. The compounds are also useful for the treatment of obesity or eating disorders associated with excessive food intake and complications associated therewith. Novel compounds of structural formula (I) are also claimed.

8 Claims, No Drawings

FOREIGN PATENT DOCUMENTS

| | | |
|---|---|---|
| WO | WO 99/02499 | 1/1999 |
| WO | WO 00/10967 | 3/2000 |
| WO | WO 00/10968 | 3/2000 |
| WO | WO 00/33836 | 6/2000 |
| WO | WO 01/28329 | 4/2001 |
| WO | WO 01/28497 | 4/2001 |
| WO | WO 01/28498 | 4/2001 |
| WO | WO 01/28557 | 4/2001 |
| WO | WO 01/29007 | 4/2001 |
| WO | WO 01/58869 | 8/2001 |
| WO | WO 01/64632 | 9/2001 |
| WO | WO 01/64633 | 9/2001 |
| WO | WO 01/64634 | 9/2001 |
| WO | WO 02/03070 | 1/2002 |
| WO | WO 02/24630 | 3/2002 |
| WO | WO 03/007887 | 1/2003 |
| WO | WO 03/027076 | 4/2003 |
| WO | WO 03/037332 | 5/2003 |
| WO | WO 03/040107 | 5/2003 |
| WO | WO 03/082191 | 10/2003 |
| WO | WO 2004/012671 | 2/2004 |
| WO | WO 2004/029204 | 4/2004 |
| WO | WO 2004/058744 | 7/2004 |
| WO | WO 2004/060870 | 7/2004 |

OTHER PUBLICATIONS

Rinaldi-Carmona et al., Life Sciences, vol. 56 (1995), pp. 1941-1947, "Biochemical and pharmacological characterisation of SR141716A, the first potent and selective brain cannabinoid receptor antagonist".

Portier et al., J. of Pharm. & Exp. Therap., vol. 288 (1999), pp. 582-589, "SR144258, an antagonist for the peripheral cannabinoid receptor that behaves as an inverse agonist".

Barth, Exp. Opin. Ther. Patents, vol. 8 (1998), pp. 301-313, "Cannabinoid receptor agonists and antgonists".

Xiang et al., Annual Reports in Medical Chemistry, vol. 34 (1999), pp. 199-208, "Chapter 20. Pharmacology of cannabinoid receptor agonists and antagonists".

Goya et al., Exp. Opin. Ther. Patents, vol. 10 (2000), pp. 1529-1538, "Recent advances in cannabinoid receptor agonists and antagonists".

Piomelli et al., Trends in Pharma. Sci., vol. 21 (2000), pp. 218-224, "The endocannabinoid system as a targent for therapeutic drugs".

Gompper et al., "Umsetzungen von Imidazolen mit Isocyanaten", CHBEAM, Chem. Ber., vol. 92, pp. 550-553 (1959).

Singh, "A convenient and new one-step synthesis of 1-imidazole-2-carboxamides", Heterocycles, vol. 34 (1992), No. 12, pp. 2373-2378.

Lange et al., J. Med. Chem. (received Jun. 4, 2004), pp. A thru P, "Bioisosteric replacement of the pyrazole moiety of rimonabant: Synthesis, biological properties, and molecular modeling investigations of thiazoles, triazoles, and imidazoles as potent and selective CB1 cannabinoid receptor antagonists".

DiMarzo et al., Emerging Ther. Targets, vol. 5 (2001), pp. 241-265, "Endocannabinoids Part I: Molecular basis of endocannabinoid formation, action and inactivation and development of selective inhibitors".

Petitet et al., Emerging Drugs, vol. 3 (1998), pp. 39-53, "The therapeutic applications of cannabinoid agonists and antagonists".

Adam et al., Expert Opin. Ther. Patents, vol. 12 (2002), pp. 1475-1489, "Recent advances in the cannabinoids".

* cited by examiner

SUBSTITUTED IMIDAZOLES AS CANNABINOID RECEPTOR MODULATORS

CROSS-REFERENCE TO RELATED APPLICATIONS

This application is a divisional application of U.S. Ser. No. 10/198,442, filed Jul. 17, 2002 now U.S. Pat. No. 7,057,051, which in turn claims priority of U.S. provisional application Ser. No. 60/307,224, filed Jul. 20, 2001.

SUMMARY OF THE INVENTION

The present invention is concerned with substituted imidazole of the general Formula I:

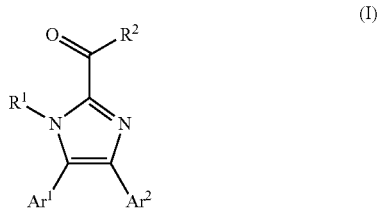

and pharmaceutically acceptable salts thereof which are antagonists and/or inverse agonists of the Cannabinoid-1 (CB1) receptor and are useful in the treatment, prevention and suppression of diseases mediated by the Cannabinoid-1 (CB1) receptor. The invention is concerned with the use of these novel compounds to selectively antagonize the Cannabinoid-1 (CB1) receptor. As such, compounds of the present invention are useful as psychotropic drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, and schizophrenia. The compounds are also useful for the treatment of substance abuse disorders, particularly to opiates, alcohol, and nicotine. The compounds are also useful for the treatment of obesity or eating disorders associated with excessive food intake and complications associated therewith.

The present invention is also concerned with treatment of these conditions, and the use of compounds of the present invention for manufacture of a medicament useful in treating these conditions.

The invention is also concerned with novel compounds of structural formula I.

The invention is also concerned with pharmaceutical formulations comprising one of the compounds as an active ingredient.

The invention is further concerned with processes for preparing the compounds of this invention.

BACKGROUND OF THE INVENTION

Marijuana (*Cannabis sativa L.*) and its derivatives have been used for centuries for medicinal and recreational purposes. A major active ingredient in marijuana and hashish has been determined to be $\Delta^9$-tetrahydrocannabinol ($\Delta^9$-THC). Detailed research has revealed that the biological action of $\Delta^9$-THC and other members of the cannabinoid family occurs through two G-protein coupled receptors termed CB1 and CB2. The CB1 receptor is primarily found in the central and peripheral nervous systems and to a lesser extent in several peripheral organs. The CB2 receptor is found primarily in lymphoid tissues and cells. Three endogenous ligands for the cannabinoid receptors derived from arachidonic acid have been identified (anandamide, 2-arachidonoyl glycerol, and 2-arachidonyl glycerol ether). Each is an agonist with activities similar to $\Delta^9$-THC, including sedation, hypothermia, intestinal immobility, antinociception, analgesia, catalepsy, anti-emesis, and appetite stimulation.

The genes for the respective cannabinoid receptors have each been disrupted in mice. The CB1$^{-/-}$ receptor knockout mice appeared normal and fertile. They were resistant to the effects of $\Delta^9$-THC and demonstrated a strong reduction in the reinforcing properties of morphine and the severity of withdrawal syndrome. They also demonstrated reduced motor activity and hypoalgesia. The CB2$^{-/-}$ receptor knockout mice were also healthy and fertile. They were not resistant to the central nervous system mediated effects of administered $\Delta^9$-THC. There were some effects on immune cell activation, reinforcing the role for the CB2 receptor in immune system functions.

Excessive exposure to $\Delta^9$-THC can lead to overeating, psychosis, hypothermia, memory loss, and sedation. Specific synthetic ligands for the cannabinoid receptors have been developed and have aided in the characterization of the cannabinoid receptors: CP55,940 (J. Pharmacol. Exp. Ther. 1988, 247, 1046-1051); WIN55212-2 (J. Pharmacol. Exp. Ther. 1993, 264, 1352-1363); SR141716A (FEBS Lett. 1994, 350, 240-244; Life Sci. 1995, 56, 1941-1947); and SR144528 (J. Pharmacol. Exp. Ther. 1999, 288, 582-589). The pharmacology and therapeutic potential for cannabinoid receptor ligands has been reviewed (Exp. Opin. Ther. Patents 1998, 8, 301-313; Ann. Rep. Med. Chem., A. Doherty, Ed.; Academic Press, NY 1999, Vol. 34, 199-208; Exp. Opin. Ther. Patents 2000, 10, 1529-1538; Trends in Pharma. Sci. 2000, 21, 218-224). There is at least one CB1 modulator characterized as an inverse agonist or an antagonist, N-(1-piperidinyl)-5-(4-chlorophenyl)-1-(2,4-dichlorophenyl)-4-methylpyrazole-3-carboxamide (SR141716A), in clinical trials for treatment of eating disorders. There still remains a need for potent low molecular weight CB1 modulators that have pharmacokinetic and pharmacodynamic properties suitable for use as human pharmaceuticals.

U.S. Pat. No. 5,624,941 and U.S. Pat. No. 6,028,084, PCT Application Nos. WO98/43636 and WO98/43635, and EPO Application No. EP-658546 disclose substituted pyrazoles having activity against the cannabinoid receptors.

PCT Application Nos. WO98/31227 and WO98/41519 also disclose substituted pyrazoles having activity against the cannabinoid receptors.

PCT Application Nos. WO98/37061, WO00/ 10967, and WO00/10968 disclose diaryl ether sulfonamides having activity against the cannabinoid receptors.

PCT Application Nos. WO97/29079 and WO99/02499 disclose alkoxy-isoindolones and alkoxy-quinolones as having activity against the cannabinoid receptors.

U.S. Pat. No. 5,532,237 discloses N-benzoyl-indole derivatives having activity against the cannabinoid receptors.

U.S. Pat. No. 4,973,587, U.S. Pat. No. 5,013,837, U.S. Pat. No. 5,081,122, and U.S. Pat. No. 5,112,820, U.S. Pat. No. 5,292,736 disclose aminoalkylindole derivatives as having activity against the cannabinoid receptors.

The compounds of the present invention are modulators of the Cannabinoid-1 (CB1) receptor and are useful in the treatment, prevention and suppression of diseases mediated by the Cannabinoid-1 (CB1) receptor. The invention is concerned with the use of these novel compounds to selectively antagonize the Cannabinoid-1 (CB1) receptor. As such, compounds of the present invention are useful as psychotropic drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, and schizophrenia. The compounds are also useful for the treatment of substance abuse disorders, particularly to opiates, alcohol, and nicotine. The compounds are also useful for the treatment of eating disorders by inhibiting excessive food intake and the resulting obesity and complications associated therewith.

DETAILED DESCRIPTION OF THE INVENTION

The compounds used in the methods of the present invention are represented by the compound of structural formula I:

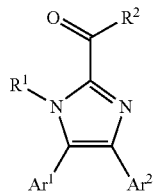

(I)

or a pharmaceutically acceptable salt thereof, wherein;
$R^1$ is selected from:
  (1) hydrogen,
  (2) $C_{1-10}$alkyl,
  (3) $C_{2-10}$alkenyl,
  (4) $C_{2-10}$alkynyl,
  (5) cycloalkyl,
  (6) cycloalkyl-$C_{1-10}$alkyl,
  (7) cycloheteroalkyl,
  (8) cycloheteroalkyl-$C_{1-10}$alkyl,
  (9) aryl,
  (10) heteroaryl,
  (11) aryl-$C_{1-10}$alkyl, and
  (12) heteroaryl-$C_{1-10}$alkyl;

wherein alkyl, alkenyl, alkynyl, and cycloalkyl are optionally substituted with one to four substituents independently selected from $R^a$, and aryl and heteroaryl are optionally substituted with one to four substituents independently selected from $R^b$;

$R^2$ is selected from:
  (1) $C_{1-10}$alkyl,
  (2) $C_{2-10}$alkenyl,
  (3) $C_{2-10}$alkynyl,
  (4) cycloalkyl,
  (5) cycloalkyl-$C_{1-10}$alkyl,
  (6) cycloheteroalkyl,
  (7) cycloheteroalkyl-$C_{1-10}$alkyl,
  (8) aryl,
  (9) heteroaryl,
  (10) aryl-$C_{1-10}$alkyl,
  (11) heteroaryl-$C_{1-10}$alkyl,
  (12) —$OR^d$,
  (13) —$NR^dR^e$, and
  (14) —$NR^dS(O)_mR^e$;

wherein alkyl, alkenyl, alkynyl, and cycloalkyl are optionally substituted with one to four substituents independently selected from $R^a$, and aryl, cycloheteroalkyl, and heteroaryl are optionally substituted with one to four substituents independently selected from $R^b$;

$Ar^1$ and $Ar^2$ are independently selected from phenyl, naphthyl, thienyl, furanyl, pyrrolyl, benzothienyl, benzofuranyl, indanyl, indenyl, indolyl, tetrahydronaphthyl, 2,3-dihydrobenzofuranyl, dihydrobenzopyranyl, and 1,4-benzodioxanyl, each optionally substituted with one or two groups independently selected from $R^c$;

each $R^a$ is independently selected from:
  (1) —$OR^d$,
  (2) —$NR^dS(O)_mR^e$,
  (3) —$NO_2$,
  (4) halogen,
  (5) —$S(O)_mR^d$,
  (6) —$SR^d$,
  (7) —$S(O)_2OR^d$,
  (8) —$S(O)_mNR^dR^e$,
  (9) —$NR^dR^e$,
  (10) —$O(CR^fR^g)_nNR^dR^e$,
  (11) —$C(O)R^d$,
  (12) —$CO_2R^d$,
  (13) —$CO_2(CR^fR^g)_nCONR^dR^e$,
  (14) —$OC(O)R^d$,
  (15) —CN,
  (16) —$C(O)NR^dR^e$,
  (17) —$NR^dC(O)R^e$,
  (18) —$OC(O)NR^dR^e$,
  (19) —$NR^dC(O)OR^e$,
  (20) —$NR^dC(O)NR^dR^e$,
  (21) —$CR^d(N—OR^e)$,
  (22) $CF_3$,
  (23) —$OCF_3$,
  (24) $C_{3-8}$cycloalkyl, and
  (25) cycloheteroalkyl;

each $R^b$ is independently selected from:
  (1) $R^a$,
  (2) $C_{1-10}$alkyl,
  (3) $C_{2-10}$alkenyl,
  (4) $C_{2-10}$alkynyl,
  (5) aryl, and
  (6) aryl-$C_{1-10}$alkyl;

wherein alkyl, alkenyl, alkynyl, and aryl are optionally substituted with one to four substituents selected from a group independently selected from $R^c$;

each $R^c$ is independently selected from:
  (1) halogen,
  (2) amino,
  (3) carboxy,
  (4) $C_{1-4}$alkyl,
  (5) $C_{1-4}$alkoxy,
  (6) aryl,
  (7) aryl $C_{1-4}$alkyl,
  (8) hydroxy,
  (9) $CF_3$,
  (10) $OC(O)C_{1-4}$alkyl,
  (11) $OC(O)NR^dR^e$, and
  (12) aryloxy;

$R^d$ and $R^e$ are independently selected from hydrogen, $C_{1-10}$alkyl, unsubstituted or substituted with one to three substituents selected from $R^h$, $C_{2-10}$alkenyl; $C_{2-10}$alkynyl; cycloalkyl, unsubstituted or substituted with one to three substituents selected from $R^h$; cycloalkyl-$C_{1-10}$alkyl; cycloheteroalkyl, unsubstituted or substituted with one to three substituents selected from R$^h$; cycloheteroalkyl-C$_{1-10}$ alkyl; aryl, unsubstituted or substituted with one to three substituents selected from R$^h$; heteroaryl, unsubstituted or substituted with one to three substituents selected from R$^h$; aryl-C$_{1-10}$alkyl; and heteroaryl-C$_{1-10}$alkyl; or R$^d$ and R$^e$ together with the atom(s) to which they are attached form a heterocyclic ring of 4 to 7 members containing 0-2 additional heteroatoms independently selected from oxygen, sulfur and N—R$^d$;

R$^f$ and R$^g$ are independently selected from hydrogen, C$_{1-10}$alkyl, C$_{2-10}$alkenyl, C$_{2-10}$alkynyl; cycloalkyl; cycloalkyl-C$_{1-10}$alkyl; cycloheteroalkyl; cycloheteroalkyl-C$_{1-10}$alkyl; aryl; heteroaryl; aryl-C$_{1-10}$alkyl; and heteroaryl-C$_{1-10}$alkyl; or R$^f$ and R$^g$ together with the carbon to which they are attached form a ring of 5 to 7 members containing 0-2 heteroatoms independently selected from oxygen, sulfur and nitrogen;

each R$^h$ is independently selected from:
(1) halogen,
(2) amino,
(3) carboxy,
(4) C$_{1-4}$alkyl,
(5) C$_{1-4}$alkoxy,
(6) aryl,
(7) aryl C$_{1-4}$alkyl,
(8) hydroxy,
(9) CF$_3$,
(10) OC(O)C$_{1-4}$alkyl, and
(11) aryloxy;

m is selected from 1 and 2; and
n is selected from 1, 2, and 3;

and pharmaceutically acceptable salts thereof.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, alkyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic or bridged saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic cycloheteroalkyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b) pyridyl, quinolyl, indolyl, isoquinolyl, and the like.

"Cycloheteroalkyl" means mono- or bicyclic or bridged saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "cycloheteroalkyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" includes fluorine, chlorine, bromine and iodine.

When any variable (e.g., R$^1$, R$^d$, etc.) occurs more than one time in any constituent or in formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a C$_{1-5}$ alkylcarbonylamino C$_{1-6}$ alkyl substituent is equivalent to

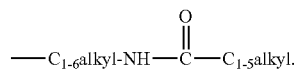

In choosing compounds of the present invention, one of ordinary skill in the art will recognize that the various substituents, i.e. R$^1$, R$^2$, etc., are to be chosen in conformity with well-known principles of chemical structure connectivity.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I or Ia may be obtained by stereospecific synthesis using optically pure starting materials or reagents of known configuration.

It is generally preferable to administer compounds of the present invention as enantiomerically pure formulations. Racemic mixtures can be separated into their individual enantiomers by any of a number of conventional methods. These include chiral chromatography, derivatization with a chiral auxillary followed by separation by chromatography or crystallization, and fractional crystallization of diastereomeric salts.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

In one embodiment of the present invention, $R^1$ is selected from:
(1) hydrogen,
(2) $C_{1-10}$alkyl,
(3) $C_{2-10}$alkenyl,
(4) $C_{2-10}$alkynyl,
(5) cycloalkyl,
(6) cycloalkyl-$C_{1-10}$alkyl,
(7) aryl-$C_{1-10}$alkyl, and
(8) heteroaryl-$C_{1-10}$alkyl;

wherein alkyl, alkenyl, alkynyl, and cycloalkyl are optionally substituted with one to four substituents independently selected from $R^a$, and aryl and heteroaryl are optionally substituted with one to four substituents independently selected from $R^b$.

In one class of this embodiment of the present invention, $R^1$ is selected from:
(1) hydrogen, and
(2) $C_{1-10}$alkyl.

In a subclass of this class of the present invention, $R^1$ is selected from:
(1) hydrogen,
(2) methyl, and
(3) ethyl.

In another subclass of this class of the present invention, $R^1$ is selected from:
(1) methyl, and
(2) ethyl.

In still another subclass of the present invention, $R^1$ is methyl.

In another embodiment of the present invention, $R^2$ is selected from:
(1) $C_{1-10}$alkyl,
(2) $C_{2-10}$alkenyl,
(3) $C_{2-10}$alkynyl,
(4) cycloalkyl,
(5) cycloalkyl-$C_{1-10}$alkyl,
(6) cycloheteroalkyl,
(7) cycloheteroalkyl-$C_{1-10}$alkyl,
(8) aryl,
(9) heteroaryl,
(10) aryl-$C_{1-10}$alkyl,
(11) heteroaryl-$C_{1-10}$alkyl,
(12) —$OR^d$, and
(13) —$NR^dR^e$, wherein alkyl, alkenyl, alkynyl, and cycloalkyl are optionally substituted with one to four substituents independently selected from $R^a$, and aryl, cycloheteroalkyl, and heteroaryl are optionally substituted with one to four substituents independently selected from $R^b$.

In one class of this embodiment of the present invention, $R^2$ is selected from:
(1) —$OR^d$, and
(2) —$NR^dR^e$.

In one subclass of this class of the invention, $R^2$ is —$NR^dR^e$.

In one embodiment of the present invention, $Ar^1$ and $Ar^2$ are independently selected from phenyl, naphthyl, thienyl, each optionally substituted with one or two groups independently selected from $R^c$;

In one class of this embodiment of the present invention, $Ar^1$ and $Ar^2$ are phenyl, each optionally substituted with one or two groups independently selected from $R^c$.

In a subclass of this class of the embodiment of the present invention, $Ar^1$ and $Ar^2$ are each independently selected from:
(1) phenyl,
(2) 4-chlorophenyl,
(3) 4-methylphenyl, and
(4) 2,4-dichlorophenyl.

In another subclass of the present invention, $Ar^1$ is 4-chlorophenyl, and $Ar^2$ is 2,4-dichlorophenyl.

In one embodiment of the present invention, each $R^a$ is independently selected from:
(1) —$OR^d$,
(2) —$NR^dS(O)_mR^e$,
(3) —$S(O)_mR^d$, (4) —$SR^d$,
(5) —$S(O)_m NR^d R^e$,
(6) —$NR^d R^e$,
(7) —$O(CR^f R^g)_n NR^d R^e$,
(8) —$CO_2 R^d$,
(9) —$CO_2(CR^f R^g)_n CONR^d R^e$,
(10) —$OC(O)R^d$,
(11) —$C(O)NR^d R^e$,
(12) —$NR^d C(O)R^e$,
(13) —$OC(O)NR^d R^e$,
(14) —$NR^d C(O)OR^e$,
(15) —$NR^d C(O)NR^d R^e$,
(16) —$CR^d(N—OR^e)$,
(17) —$CF_3$, and
(18) —$OCF_3$.

In another embodiment of the present invention, each $R^b$ is independently selected from:
(1) $R^a$,
(2) halogen,
(3) —CN,
(4) $C_{1-10}$ alkyl,
(5) $C_{2-10}$ alkenyl,
(6) $C_{2-10}$ alkynyl,
(7) aryl, and
(8) aryl-$C_{1-10}$alkyl;

wherein alkyl, alkenyl, alkynyl, and aryl are optionally substituted with one to four substituents selected from a group independently selected from $R^c$;

In one embodiment of the present invention, each $R^c$ is independently selected from:
(1) halogen,
(2) —$NR^d R^e$,
(3) $C_{1-4}$alkyl,
(4) $C_{1-4}$alkoxy,
(5) aryl $C_{1-4}$alkyl,
(6) hydroxy,
(7) $CF_3$,
(8) —$OCF_3$,
(9) —$CO_2 R^d$,
(10) —$C(O)NR^d R^e$, and
(11) —$NR^d C(O)R^e$.

In a class of the present invention, each $R^c$ is independently selected from:
(1) halogen,
(2) $C_{1-4}$alkyl, and
(3) $CF_3$.

In one subclass of this class of the present invention, each $R^c$ is independently selected from:
(1) chloro,
(2) fluoro,
(3) methyl, and
(4) $CF_3$.

In one embodiment of the present invention, $R^d$ and $R^e$ are independently selected from hydrogen, $C_{1-10}$alkyl, cycloalkyl; cycloalkyl-$C_{1-10}$alkyl; cycloheteroalkyl; cycloheteroalkyl-$C_{1-10}$alkyl; aryl; heteroaryl; aryl-$C_{1-10}$alkyl; and heteroaryl-$C_{1-10}$alkyl; or $R^d$ and $R^e$ together with the atom(s) to which they are attached form a heterocyclic ring of 4 to 7 members containing 0-2 additional heteroatoms independently selected from oxygen, sulfur and N—$R^d$.

In one class of this embodiment of the present invention, $R^d$ and $R^e$ are independently selected from hydrogen, $C_{1-10}$alkyl; cycloalkyl; cycloalkyl-$C_{1-10}$alkyl; cycloheteroalkyl; cycloheteroalkyl-$C_{1-10}$alkyl; aryl; heteroaryl; aryl-$C_{1-10}$alkyl; and heteroaryl-$C_{1-10}$alkyl; or $R^d$ and $R^e$ together with the nitrogen to which they are attached form a heterocyclic ring of 4 to 7 members containing 0-1 additional heteroatoms independently selected from oxygen, sulfur and N—$R^d$.

In a subclass of this class of the present invention, $R^d$ is selected from hydrogen, methyl, ethyl, n-propyl, isopropyl, butyl, t-butyl, n-hexyl, cyclohexyl, cycloheptyl, piperidinyl, morpholinyl, pyrrolidinyl, cycloheteroalkyl, phenyl and benzyl; $R^e$ is selected from hydrogen and methyl; or $R^d$ and $R^e$ together with the nitrogen to which they are attached form a piperidinyl, pyrrolidinyl, or morpholinyl ring.

In yet another subclass of this class of the present invention, $R^d$ is selected from hydrogen, methyl, ethyl, n-propyl, isopropyl, butyl, t-butyl, n-hexyl, cyclohexyl, cycloheptyl, piperidinyl, morpholinyl, pyrrolidinyl, cycloheteroalkyl, phenyl and benzyl; $R^e$ is selected from hydrogen and methyl; or $R^d$ and $R^e$ together with the nitrogen to which they are attached form a piperidinyl, pyrrolidinyl, or morpholinyl ring.

In another subclass of this class of the present invention, $R^d$ is selected from cyclohexyl, cycloheptyl, piperidinyl, morpholinyl, pyrrolidinyl, phenyl and benzyl;

$R^e$ is hydrogen; or $R^d$ and $R^e$ together with the nitrogen to which they are attached form a piperidinyl, or pyrrolidinyl ring.

In yet another subclass of the present invention, $R^d$ is selected from cyclohexyl and 1-piperidinyl; and $R^e$ is hydrogen.

In one embodiment of the present invention, $R^f$ and $R^g$ are independently selected from hydrogen, $C_{1-10}$alkyl, cycloalkyl; cycloalkyl-$C_{1-10}$ alkyl; cycloheteroalkyl; cycloheteroalkyl-$C_{1-10}$ alkyl; aryl; heteroaryl; aryl-$C_{1-10}$ alkyl; and heteroaryl-$C_{1-10}$ alkyl; or $R^f$ and $R^g$ together with the carbon to which they are attached form a ring of 5 to 7 members containing 0-2 heteroatoms independently selected from oxygen, sulfur and nitrogen.

In one embodiment of the present invention, each $R^h$ is independently selected from:
(1) halogen,
(2) $C_{1-4}$alkyl,
(3) $C_{1-4}$alkoxy,
(4) aryl $C_{1-4}$alkyl,
(5) hydroxy,
(6) $CF_3$,
(7) —$OCF_3$,
(8) —$CO_2 R^d$, and
(9) —$C(O)NR^d R^e$;

In a class of the present invention, each $R^h$ is independently selected from:
(1) halogen,
(2) $C_{1-4}$alkyl, and
(3) $CF_3$.

In one subclass of this class of the present invention, each $R^h$ is independently selected from:
(1) chloro,
(2) fluoro,
(3) methyl, and
(4) $CF_3$.

Particular novel compounds which may be employed in the methods, uses and compositions of the present invention, include:
(1) benzyl 4,5-diphenyl-1-methylimidazole-2-carboxylate,
(2) benzyl 4,5-di-(4-methylphenyl)-1-methylimidazole-2-carboxylate,
(3) ethyl 4,5-di-(4-methylphenyl)-1-methylimidazole-2-carboxylate,
(4) N-(piperidin-1-yl)-4,5-diphenyl-1-methylimidazole-2-carboxamide, (5) 2-(piperidin-1-ylcarbonyl)-4,5-diphenyl-1-methylimidazole,
(6) N-(morpholin-4-yl)-4,5-diphenyl-1-methylimidazole-2-carboxamide,
(7) N-phenyl-4,5-diphenyl-1-methylimidazole-2-carboxamide,
(8) N-hexyl-4,5-diphenyl-1-methylimidazole-2-carboxamide,
(9) N-cyclohexyl-4,5-diphenyl-1-methylimidazole-2-carboxamide,
(10) N-(piperidin-1-yl)-4,5-di-(4-methylphenyl)-1-methylimidazole-2-carboxamide,
(11) 2-(piperidin-1-ylcarbonyl)-4,5-di-(4-methylphenyl)-1-methylimidazole,
(12) N-(morpholin-4-yl)-4,5-di-(4-methylphenyl)-1-methylimidazole-2-carboxamide,
(13) 2-(pyrrolidin-1-ylcarbonyl)-4,5-di-(4-methylphenyl)-1-methylimidazole,
(14) N-benzyl-4,5-di-(4-methylphenyl)-1-methylimidazole-2-carboxamide,
(15) N-phenyl-4,5-di-(4-methylphenyl)-1-methylimidazole-2-carboxamide,
(16) N-hexyl-4,5-di-(4-methylphenyl)-1-methylimidazole-2-carboxamide,
(17) N-t-butyl-4,5-di-(4-methylphenyl)-1-methylimidazole-2-carboxamide,
(18) N-cyclohexyl-4,5-di-(4-methylphenyl)-1-methylimidazole-2-carboxamide,
(19) N-propyl-4,5-di-(4-methylphenyl)-1-methylimidazole-2-carboxamide,
(20) N-methyl-4,5-di-(4-methylphenyl)-1-methylimidazole-2-carboxamide,
(21) benzyl 4,5-di-(4-chlorophenyl)-1-methylimidazole-2-carboxylate,
(22) N-(piperidin-1-yl)-4,5-di-(4-chlorophenyl)-1-methylimidazole-2-carboxamide,
(23) 2-(piperidin-1-ylcarbonyl)-4,5-di-(4-chlorophenyl)-1-methylimidazole,
(24) N-(morpholin-1-yl)-4,5-di-(4-chlorophenyl)-1-methylimidazole-2-carboxamide,
(25) N-(hexyl)-4,5-di-(4-chlorophenyl)-1-methylimidazole-2-carboxamide,
(26) N-(t-butyl)-4,5-di-(4-chlorophenyl)-1-methylimidazole-2-carboxamide,
(27) N-(cyclohexyl)-4,5-di-(4-chlorophenyl)-1-methylimidazole-2-carboxamide,
(28) N-hexyl-4,5-di-(4-chlorophenyl)imidazole-2-carboxamide,
(29) N-cyclohexyl-4,5-di-(4-chlorophenyl)imidazole-2-carboxamide,
(30) N-t-butyl-4,5-di-(4-chlorophenyl)imidazole-2-carboxamide,
(31) benzyl 4,5-di-(4-chlorophenyl)-1-(2-(trimethylsilyl)ethoxymethyl)imidazole-2-carboxylate,
(32) N-(piperidin-1-yl)-4,5-di-(4-chlorophenyl)imidazole-2-carboxamide,
(33) N-(piperidin-1-yl)-4,5-di-(2,4-dichlorophenyl)-1-methylimidazole-2-carboxamide,
(34) N-(cyclohexyl)-4,5-di-(2,4-dichlorophenyl)-1-methylimidazole-2-carboxamide,
(35) N-(piperidin-1-yl)-4-(4-chlorophenyl)-5-(2,4-dichlorophenyl)-1-methylimidazole-2-carboxamide,
(36) N-(cyclohexyl)-4-(4-chlorophenyl)-5-(2,4-dichlorophenyl)-1-methylimidazole-2-carboxamide,
(37) N-(hexyl)-4-(4-chlorophenyl)-5-(2,4-dichlorophenyl)-1-methylimidazole-2-carboxamide,
(38) N-(t-butyl)-4-(4-chlorophenyl)-5-(2,4-dichlorophenyl)-1-methylimidazole-2-carboxamide,
(39) N-(cyclohexyl)-4-(2,4-dichlorophenyl)-5-(4-chlorophenyl)-1-methylimidazole-2-carboxamide,
(40) N-(piperidin-1-yl)-4-(2,4-dichlorophenyl)-5-(4-chlorophenyl)-1-methylimidazole-2-carboxamide,
(41) N-(cycloheptyl)-4-(2,4-dichlorophenyl)-5-(4-chlorophenyl)-1-methylimidazole-2-carboxamide,
(42) N-(cyclopentyl)-4-(2,4-dichlorophenyl)-5-(4-chlorophenyl)-1-methylimidazole-2-carboxamide,
(43) N-(morpholin-4-yl)-4-(2,4-dichlorophenyl)-5-(4-chlorophenyl)-1-methylimidazole-2-carboxamide,
(44) N-(phenyl)-4-(2,4-dichlorophenyl)-5-(4-chlorophenyl)-1-methylimidazole-2-carboxamide,
(45) N-(piperidin-1-yl)-4-(4-chlorophenyl)-5-(2,4-dichlorophenyl)-1-ethylimidazole-2-carboxamide,
(46) N-(cyclohexyl)-4-(4-chlorophenyl)-5-(2,4-dichlorophenyl)-1-ethylimidazole-2-carboxamide,
(47) N-(hexyl)-4-(4-chlorophenyl)-5-(2,4-dichlorophenyl)-1-ethylimidazole-2-carboxamide,
(48) N-(cyclohexyl)-4-(2,4-dichlorophenyl)-5-(4-chlorophenyl)-1-ethylimidazole-2-carboxamide,
(49) cyclohexyl 4-(2,4-dichlorophenyl)-5-(4-chlorophenyl)-1-methylimidazole-2-carboxylate,
(50) N-methyl-N-cyclohexyl-4-(2,4-dichlorophenyl)-5-(4-chlorophenyl)-1-methylimidazole-2-carboxylate,
(51) ethyl 4-(2,4-dichlorophenyl)-5-(4-chlorophenyl)-1-methylimidazole-2-carboxylate,
(52) N-(cyclohexyl)-4-(2,4-dichlorophenyl)-5-(4-chlorophenyl)-1-ethylimidazole-2-carboxamide,
(53) N-(cyclohexyl)-4-(2,4-dichlorophenyl)-5-(4-chlorophenyl)-1-(1-methyl)ethyl-imidazole-2-carboxamide,
(54) N-(cyclohexyl)-4-(2,4-dichlorophenyl)-5-(4-chlorophenyl)-1-(1,1-dimethyl)ethyl-imidazole-2-carboxamide,
(55) N-(cyclohexyl)-4-(2,4-dichlorophenyl)-5-(4-chlorophenyl)-1-(2-dimethylamino)ethylimidazole-2-carboxamide,
(56) N-(cyclohexyl)-4-(2,4-dichlorophenyl)-5-(4-chlorophenyl)-1-butylimidazole-2-carboxamide,
(57) N-(cyclohexyl)-4-(2,4-dichlorophenyl)-5-(4-chlorophenyl)-1-(2-methoxy)ethylimidazole-2-carboxamide,
(58) N-(piperidin-1-yl)-5-(4-chlorophenyl)-4-(2,4-dichlorophenyl)-1-methyl-imidazole-2-carboxamide,
(59) N-(pyrrolidin-1-yl)-5-(4-chlorophenyl)-4-(2,4-dichlorophenyl)-1-methyl-imidazole-2-carboxamide,
(60) N-(azepin-1-yl)-5-(4-chlorophenyl)-4-(2,4-dichlorophenyl)-1-methyl-imidazole-2-carboxamide,
(61) N-(pentyl)-4-(2,4-dichlorophenyl)-5-(4-chlorophenyl)-1-methylimidazole-2-carboxamide,
(62) N-(1-ethylpropyl)-4-(2,4-dichlorophenyl)-5-(4-chlorophenyl)-1-methylimidazole-2-carboxamide,
(63) N-(1-methylethyl)-4-(2,4-dichlorophenyl)-5-(4-chlorophenyl)-1-methylimidazole-2-carboxamide,
(64) N-(3-cyclohexenyl)-4-(2,4-dichlorophenyl)-5-(4-chlorophenyl)-1-methylimidazole-2-carboxamide,
(65) N-(tetrahydropyran-4-yl)-4-(2,4-dichlorophenyl)-5-(4-chlorophenyl)-1-methylimidazole-2-carboxamide,
(66) N-(2,2-dimethyl-tetrahydropyran-4-yl)-4-(2,4-dichlorophenyl)-5-(4-chlorophenyl)-1-methylimidazole-2-carboxamide,
(67) N-((2-trans-hydroxymethyl)cyclohexyl)-4-(2,4-dichlorophenyl)-5-(4-chlorophenyl)-1-methylimidazole-2-carboxamide,
(68) N-((2-cis-hydroxymethyl)cyclohexyl)-4-(2,4-dichlorophenyl)-5-(4-chlorophenyl)-1-methylimidazole-2-carboxamide,

(69) N-((2-trans-hydroxy)cyclohexyl)-4-(2,4-dichlorophenyl)-5-(4-chlorophenyl)-1-methylimidazole-2-carboxamide,
(70) N-((2-cis-hydroxy)cyclohexyl)-4-(2,4-dichlorophenyl)-5-(4-chlorophenyl)-1-methylimidazole-2-carboxamide,
(71) N-((4-trans-hydroxy)cyclohexyl)-4-(2,4-dichlorophenyl)-5-(4-chlorophenyl)-1-methylimidazole-2-carboxamide,
(72) N-(4-methyl-cyclohexyl)-4-(2,4-dichlorophenyl)-5-(4-chlorophenyl)-1-methylimidazole-2-carboxamide(Isomer A),
(73) N-(4-methyl-cyclohexyl)-4-(2,4-dichlorophenyl)-5-(4-chlorophenyl)-1-methylimidazole-2-carboxamide(Isomer B),
(74) N-(1-fluoro-cyclohexen-4-yl)-4-(2,4-dichlorophenyl)-5-(4-chlorophenyl)-1-methylimidazole-2-carboxamide,
(75) N-(4,4-difluoro-cyclohexyl)-4-(2,4-dichlorophenyl)-5-(4-chlorophenyl)-1-methylimidazole-2-carboxamide,
(76) 4-(2,4-dichlorophenyl)-5-(4-chlorophenyl)-1-methylimidazole-2-carboxamide,
(77) N-(piperidin-1-yl)-5-(4-chlorophenyl)-4-(2,4-dichlorophenyl)-1-ethyl-imidazole-2-carboxamide,
(78) N-(piperidin-1-yl)-5-(4-chlorophenyl)-4-(2,4-dichlorophenyl)-1-(1-methyl)ethyl-imidazole-2-carboxamide,
(79) N-(piperidin-1-yl)-5-(4-chlorophenyl)-4-(2,4-dichlorophenyl)-1-(1,1-dimethyl)ethyl-imidazole-2-carboxamide,
(80) N-(piperidin-1-yl)-5-(4-chlorophenyl)-4-(2,4-dichlorophenyl)-1-(2-dimethylamino)ethyl-imidazole-2-carboxamide,
(81) N-(piperidin-1-yl)-5-(4-chlorophenyl)-4-(2,4-dichlorophenyl)-1-propyl-imidazole-2-carboxamide,
(82) N-(piperidin-1-yl)-5-(4-chlorophenyl)-4-(2,4-dichlorophenyl)-1-butyl-imidazole-2-carboxamide,
(83) N-(piperidin-1-yl)-5-(4-chlorophenyl)-4-(2,4-dichlorophenyl)-1-(2-methoxy)ethyl-imidazole-2-carboxamide,
(84) N-(cyclohexyl)-4-(2-chlorophenyl)-5-(4-chlorophenyl)-1-methylimidazole-2-carboxamide,
(85) N-(piperidin-1-yl)-4-(2-chlorophenyl)-5-(4-chlorophenyl)-1-methyl-imidazole-2-carboxamide, and pharmaceutically acceptable salts thereof.

In one embodiment of the present invention, a compound selected from the following novel compounds is employed:
(1) N-(cyclohexyl)-4-(2,4-dichlorophenyl)-5-(4-chlorophenyl)-1-methylimidazole-2-carboxamide,
(2) N-(cyclohexyl)-4-(2,4-dichlorophenyl)-5-(4-chlorophenyl)-1-ethylimidazole-2-carboxamide,
(3) N-(piperidin-1-yl)-4-(2,4-dichlorophenyl)-5-(4-chlorophenyl)-1-methylimidazole-2-carboxamide,
(4) N-(cyclohexyl)-4,5-di-(2,4-dichlorophenyl)-1-methylimidazole-2-carboxamide,
(5) N-(cycloheptyl)-4-(2,4-dichlorophenyl)-5-(4-chlorophenyl)-1-methylimidazole-2-carboxamide,
(6) N-(piperidin-1-yl)-4,5-di-(2,4-dichlorophenyl)-1-methylimidazole-2-carboxamide,
(7) N-(cyclopentyl)-4-(2,4-dichlorophenyl)-5-(4-chlorophenyl)-1-methylimidazole-2-carboxamide, and pharmaceutically acceptable salts thereof.

In one class of this embodiment, a compound selected from the following novel compounds is employed;
(1) N-(cyclohexyl)-4-(2,4-dichlorophenyl)-5-(4-chlorophenyl)-1-methylimidazole-2-carboxamide,
(2) N-(piperidin-1-yl)-4-(2,4-dichlorophenyl)-5-(4-chlorophenyl)-1-methylimidazole-2-carboxamide,
(3) N-(cyclohexyl)-4,5-di-(2,4-dichlorophenyl)-1-methylimidazole-2-carboxamide, and pharmaceutically acceptable salts thereof.

Compounds of this invention are modulators of the CB1 receptor and as such are useful for the prevention and treatment of disorders or diseases associated with the CB1 receptor. Accordingly, another aspect of the present invention provides a method for the treatment (including prevention, alleviation, amelioration or suppression) of diseases or disorders or symptoms mediated by CB1 receptor binding and subsequent cell activation, which comprises administering to a mammal an effective amount of a compound of Formula I. Such diseases, disorders, conditions or symptoms are, for example, psychosis, memory deficits, cognitive disorders, migraine, neuropathy, anxiety disorders, depression, stress, epilepsy, Parkinson's disease, schizophrenia, substance use disorders, particularly to opiates, alcohol, and nicotine, obesity, and eating disorders associated with excessive food intake and the resulting obesity and complications associated therewith.

The terms "administration of" and or "administering a" compound should be understood to mean providing a compound of the invention or a prodrug of a compound of the invention to the individual in need of treatment.

The administration of the compound of structural formula I in order to practice the present methods of therapy is carried out by administering an effective amount of the compound of structural formula I to the patient in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The utilities of the present compounds in these diseases or disorders may be demonstrated in animal disease models that have been reported in the literature. The following are examples of such animal disease models: a) suppression of food intake and resultant weight loss in rats (Life Sciences 1998, 63, 113-117); b) reduction of sweet food intake in marmosets (Behavioural Pharm. 1998, 9, 179-181); c) reduction of sucrose and ethanol intake in mice (Psychopharm. 1997, 132, 104-106); d) increased motor activity and place conditioning in rats (Psychopharm. 1998, 135, 324-332; Psychopharmacol 2000, 151: 25-30); e) spontaneous locomotor activity in mice (J. Pharm. Exp. Ther. 1996, 277, 586-594); f) reduction in opiate self-administration in mice (Sci. 1999, 283, 401-404);

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg)

of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per day, preferably from about 0.1 mg to about 10 mg per day. For oral administration, the compositions are preferably provided in the form of tablets containing from 0.01 to 1,000 mg, preferably 0.01, 0.05, 0.1, 0.5, 1.0, 2.5, 5.0, 10.0, 15.0, 20.0, 25.0, 30.0, 40.0, 50.0 or 1000.0 milligrams of the active ingredient for the symptomatic adjustment of the dosage to the patient to be treated.

For the treatment of diseases of the eye, ophthalmic preparations for ocular administration comprising 0.001-1% by weight solutions or suspensions of the compounds of Formula I in an acceptable ophthalmic formulation may be used.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), preferably present in pharmaceutically effective amounts, and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The term "pharmaceutically effective amount" of an active ingredient such as a compound of structural formula I, it is intended to encompass amounts of the ingredient that are therapeutically or prophylatically useful in treating or preventing disease, particularly diseases associated with modulation of the Cannabinoid 1 receptor.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, suppositories and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. In particular, the term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like. Topical preparations containing the active drug component can be admixed with a variety of carrier materials well known in the art such as, e.g., alcohols, aloe vera gel, allantoin, glycerine, vitamin A and E oils, mineral oil, PPG2 myristyl propionate, and the like. To be administered in the form of a transdermal delivery system, the dosage administration will, of course, be continuous rather than intermittent throughout the dosage regimen.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, sterylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide phenol, polyhydroxyethylasparamidepheon, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxybutyric acid, polyorthoesters, polyacetals, polydihydropyrans, polycyanoacrylates and cross-linked or amphipathic block copolymers of hydrogels.

Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from 0.01 to 500 mg, particularly 0.01, 0.05, 0.1, 0.5, 1.0, 2.5, 3.0, 5.0, 6.0, 10.0, 15.0, 25.0, 50.0, 75, 100, 125, 150, 175, 180, 200, 225, and 500 milligrams of the active ingredient for the symptomatic adjustment of the dosage to the patient to be treated and each cachet or capsule contains from about 0.01 to 500 mg, particularly 0.01, 0.05, 0.1, 0.5, 1.0, 2.5, 3.0, 5.0, 6.0, 10.0, 15.0, 25.0, 50.0, 75, 100, 125, 150, 175, 180, 200, 225, and 500 milligrams of the active ingredient for the symptomatic adjustment of the dosage to the patient to be treated.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

Injectable Suspension (I.M.) mg/mL

| Compound of Formula I | 10 |
|---|---|
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:

It will be appreciated that for the treatment or prevention of eating disorders, including obesity, bulimia nervosa and compulsive eating disorders, a compound of the present invention may be used in conjunction with other anorectic agents.

The present invention also provides a method for the treatment or prevention of eating disorders, which method comprises administration to a patient in need of such treatment an amount of a compound of the present invention and an amount of an anorectic agent, such that together they give effective relief.

Suitable anoretic agents of use in combination with a compound of the present invention include, but are not limited to, aminorex, amphechloral, amphetamine, benzamphetamine, chlorphentemine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof.

Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention also provides a method for the treatment or prevention of obesity, which method comprises administration to a patient in need of such treatment an amount of a compound of the present invention and an amount of an SSRI, such that together they give effective relief.

Suitable selective serotonin reuptake inhibitors of use in combination with a compound of the present invention include: fluoxetine, fluvoxamine, paroxetine and sertraline, and pharmaceutically acceptable salts thereof.

The present invention also provides a method for the treatment or prevention of obesity, which method comprises administration to a patient in need of such treatment an amount of a compound of the present invention and an amount of growth hormone secretagogues such as those disclosed and specifically described in U.S. Pat. No. 5,536,716; melanocortin agonists such as Melanotan II or those described in WO 99/64002 and WO 00/74679; β-3 agonists such as those disclosed and specifically described in patent publications WO94/18161, WO95/29159, WO97/46556, WO98/04526 and WO98/32753; 5HT-2 agonists; orexin antagonists; melanin concentrating hormone antagonists; galanin antagonists; CCK agonists; GLP-1 agonists; corticotropin-releasing hormone agonists; NPY-5 antagonists; and Y1 antagonists, such that together they give effective relief As used herein "obesity" refers to a condition whereby a mammal has a Body Mass Index (BMI), which is calculated as weight per height squared ($kg/m^2$), of at least 25.9. Conventionally, those persons with normal weight, have a BMI of 19.9 to less than 25.9.

It will be appreciated that for the treatment or prevention of obesity, the compounds of the present invention may also be used in combination with histamine receptor-3 (H3) modulators, melanin concentrating hormone-1receptor (MCH1R) antagonists, melanin concentrating hormone-2 receptor (MCH2R) agonists and antagonists and/or phosphodiesterase-3B (PDE3B) inhibitors.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia.

"Treatment" (of obesity) refers to reducing the BMI of the mammal to less than about 25.9, and maintaining that weight for at least 6 months. The treatment suitably results in a reduction in food or calorie intake by the mammal.

"Prevention" (of obesity) refers to preventing obesity from occurring if the treatment is administered prior to the onset of the obese condition. Moreover, if treatment is commenced in already obese subjects, such treatment is expected to present, or to prevent the progression of, the medical sequelae of obesity, such as, e.g., arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

It will be appreciated that for the treatment or prevention of migraine, a compound of the present invention may be used in conjunction with other anti-migraine agents, such as ergotamines or $5-HT_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents.

Suitable classes of anti-depressant agents include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, (α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agents include benzodiazepines and $5-HT_{1A}$ agonists or antagonists, especially $5-HT_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-HT$_{1A}$ receptor agonists or antagonists include, in particular, the 5-HT$_{1A}$ receptor partial agonists buspirone, flesinoxan, gepirone and ipsapirone, and pharmaceutically acceptable salts thereof.

As used herein, the term "substance abuse disorders" includes substance dependence or abuse with or without physiological dependence. The substances associated with these disorders are: alcohol, amphetamines (or amphetamine-like substances), caffeine, cannabis, cocaine, hallucinogens, inhalants, nicotine, opioids, phencyclidine (or phencyclidine-like compounds), sedative-hypnotics or benzodiazepines, and other (or unknown) substances and combinations of all of the above.

In particular, the term "substance abuse disorders" includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation.

Other "substance abuse disorders" include substance-induced anxiety disorder with onset during withdrawal; substance-induced mood disorder with onset during withdrawal; and substance-induced sleep disorder with onset during withdrawal.

It will be appreciated that a combination of a conventional antipsychotic drug with a CB1 receptor modulator may provide an enhanced effect in the treatment of mania. Such a combination would be expected to provide for a rapid onset of action to treat a manic episode thereby enabling prescription on an "as needed basis". Furthermore, such a combination may enable a lower dose of the antipsychotic agent to be used without compromising the efficacy of the antipsychotic agent, thereby minimising the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

Thus, according to a further aspect of the present invention there is provided the use of a CB1 receptor modulator and an antipsychotic agent for the manufacture of a medicament for the treatment or prevention of mania.

The present invention also provides a method for the treatment or prevention of mania, which method comprises administration to a patient in need of such treatment of an amount of a CB1 receptor modulator and an amount of an antipsychotic agent, such that together they give effective relief.

In a further aspect of the present invention, there is provided a pharmaceutical composition comprising a CB1 receptor modulator and an antipsychotic agent, together with at least one pharmaceutically acceptable carrier or excipient.

It will be appreciated that the CB1 receptor modulator and the antipsychotic agent may be present as a combined preparation for simultaneous, separate or sequential use for the treatment or prevention of mania. Such combined preparations may be, for example, in the form of a twin pack.

In a further or alternative aspect of the present invention, there is therefore provided a product comprising a CB1 receptor modulator and an antipsychotic agent as a combined preparation for simultaneous, separate or sequential use in the treatment or prevention of mania.

It will be appreciated that when using a combination of the present invention, the CB1 receptor modulator and the antipsychotic agent may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, the antipsychotic agent may be administered as a tablet and then, within a reasonable period of time, the CB1 receptor modulator may be administered either as an oral dosage form such as a tablet or a fast-dissolving oral dosage form. By a "fast-dissolving oral formulation" is meant, an oral delivery form which when placed on the tongue of a patient, dissolves within about 10 seconds.

Included within the scope of the present invention is the use of CB1 receptor modulators in combination with an antipsychotic agent in the treatment or prevention of hypomania.

Suitable antipsychotic agents of use in combination with a CB1 receptor modulator include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a CB1 receptor modulator may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

It will be appreciated that a combination of a conventional antipsychotic drug with a CB1 receptor modulator may provide an enhanced effect in the treatment of schizophrenic disorders. Such a combination would be expected to provide for a rapid onset of action to treat schizophrenic symptoms thereby enabling prescription on an "as needed basis". Furthermore, such a combination may enable a lower dose of the CNS agent to be used without compromising the efficacy of the antipsychotic agent, thereby minimising the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

As used herein, the term "schizophrenic disorders" includes paranoid, disorganized, catatonic, undifferentiated and residual schizophrenia; schizophreniform disorder; schizoaffective disorder; delusional disorder; brief psychotic disorder; shared psychotic disorder; substance-induced psychotic disorder; and psychotic disorder not otherwise specified.

Other conditions commonly associated with schizophrenic disorders include self-injurious behavior (e.g. Lesch-Nyhan syndrome) and suicidal gestures.

Suitable antipsychotic agents of use in combination with a CB1 receptor modulator include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a CB1 receptor modulator may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agent of use in combination with a CB1 receptor modulator include dopamine receptor antagonists, especially D2, D3 and D4 dopamine receptor antagonists, and muscarinic m1 receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with a CB1 receptor modulator is the 5-HT$_{2A}$ receptor antagonists, examples of which include MDL100907 and fananserin. Also of use in combination with a CB1 receptor modulator are the serotonin dopamine antagonists (SDAs) which are believed to combine 5-HT$_{2A}$ and dopamine receptor antagonist activity, examples of which include olanzapine and ziperasidone.

The method of treatment of this invention comprises a method of modulating the CB1 receptor and treating CB1 receptor mediated diseases by administering to a patient in need of such treatment a non-toxic therapeutically effective amount of a compound of this invention that selectively antagonizes the CB1 receptor in preference to the other CB or G-protein coupled receptors.

The term "therapeutically effective amount" means the amount the compound of structural formula I that will elicit the biological or medical response of a tissue, system, animal or human that is being sought by the researcher, veterinarian, medical doctor or other clinician.

The weight ratio of the compound of the Formula I to the second active ingredient may be varied and will depend upon the effective dose of each ingredient. Generally, an effective dose of each will be used. Thus, for example, when a compound of the Formula I is combined with a β-3 agonist the weight ratio of the compound of the Formula I to the β-3 agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Abbreviations used in the following Schemes and Examples:
4-DMAP: 4-dimethylaminopyridine
Ac$_2$O: acetic anhydride
AcCN: acetonitrile
Ag$_2$O: silver(I) oxide
AIBN: 2,2'-azobisisobutyronitrile
BF$_3$-Et$_2$O: borontrifluoride etherate
BH$_3$-DMS: borane dimethylsulfide complex
Bn: benzyl
BOC: tert-butoxycarbonyl
BOC-ON 2-(tert-butoxycarbonyloxyimino)-2-phenylacetonitrile
BOP: benzotriazol-1-yloxy-tris(dimethylamino)-phosphonium hexafluorophosphate
brine: saturated sodium chloride solution
CBZ: benzyloxycarbonyl
Cy$_3$P: tricyclohexylphosphine
DBU: 1,8-diazobicyclo[5.4.0]undec-7-ene
DCC: dicyclohexylcarbodiimide
DIBAL-H: diisobutylaluminum hydride
DIPEA: N,N-diisopropylethylamine
DME: 1,2-dimethoxyethane
DMF: dimethylformamide
DMPU: 1,3-dimethyl-3,4,5,6-tetrahydro-2(1H)-pyrimidinone
DMSO: dimethylsulfoxide
EDC: 1-ethyl-3-(3-dimethylaminopropyl)-carbodiimide hydrochloride
Et: ethyl
Et$_2$O: diethyl ether
EtOAc: ethyl acetate
EtOH: ethanol
FMOC: 9-fluorenylmethoxylcarbonyl
g or gm: gram
h or hr: hours
HATU: O-(7-azabenzotriazol-1-yl)-1,1,3,3-tetramethyluronium hexafluorophosphate
HBTU: O-(benzotriazol-1-yl)-1,1,3,3-tetramethyluronium hexafluorophosphate
HOAc: acetic acid
HOAt: 1-hydroxy-7-azabenzotriazole
HOBt: 1-hydroxybenzotriazole
HPLC: high pressure liquid chromatography
in vacuo: rotoevaporation
KOAc: potassium acetate
LDA: lithium diisopropylamide
LiHMDS: lithium hexamethyldisilylamide
mCPBA: meta-chloroperbenzoic acid
Me: methyl
MeI: methyl iodide
MeOH: methanol
mg: milligram
MHz: megahertz
min: minutes
mL: milliliter
mmol: millimole
MPLC: medium pressure liquid chromatography
MS or ms: mass spectrum
MsCl: methanesulfonyl chloride
NBS: N-bromosuccinimide
n-Bu n-butyl
NMO: 4-methyl-morpholine-N-oxide
Pd$_2$dba$_3$: tris(dibenzylideneacetone)dipalladium(0)
Ph: phenyl
Ph$_3$P: triphenylphosphine
pTSA: para-toluenesulfonic acid
PyBOP: (benzotriazol-1-yloxy)tripyrrolidinophosphonium hexafluorophosphate
rt: room temperature TBAF: tetrabutylammonium fluoride
TBSCl: tert-butyldimethylsilyl chloride
t-Bu₃P: tri-tert-butylphosphine
TEA: triethylamine
TFA: trifluoroacetic acid
THF: THF
TLC: thin layer chromatography
TMSCHN$_2$: trimethylsiliyldiazomethane
TMSCl: trimethylsilyl chloride
TMSI: trimethylsilyl iodide
TPAP: tetrapropylammonium perruthenate
TsCl: para-toluene sulfonyl chloride Compounds of the present invention may be prepared by procedures illustrated in the accompanying schemes.

As outlined in Scheme 1, benzoin derivatives A are condensed with urea B in heated ethylene glycol to afford 2(3H)-imidazolone C. Typically, a mixture of the two regioisomers is obtained that may or may not be separated. Treatment of C with phosphorous oxychloride affords the 2-chloro-imidazoles D. Lithiation of D with n-butyllithium followed by acylation yields the imidazole-2-carboxylate E. The ester in E is hydrogenated (R²=benzyloxy) or hydrolyzed (R²=ethoxy or benzyloxy) to afford carboxylic acid F. Coupling with an amine derivative in the presence of a coupling agent yields the imidazole-2-carboxamides G. Alternatively, ester E may be heated neat with an amine to afford G directly. G may be obtained directly from D by lithiation with n-butyllithium followed by acylation with an isocyanate.

Alternatively, as shown in Scheme 2, benzil derivative A or benzoin derivative B are condensed with formamide and paraformaldehyde to afford diaryl-imidazole C. Treatment with base (e.g., sodium hydride) followed by treatment with an electrophile affords N-substituted imidazole D. Reaction with n-butyllithium followed by acylation yields imidazole-2-carboxylates E which may be treated as outlined in Scheme 1.

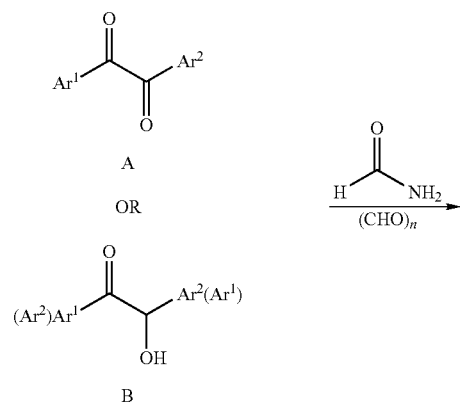

Scheme 2.

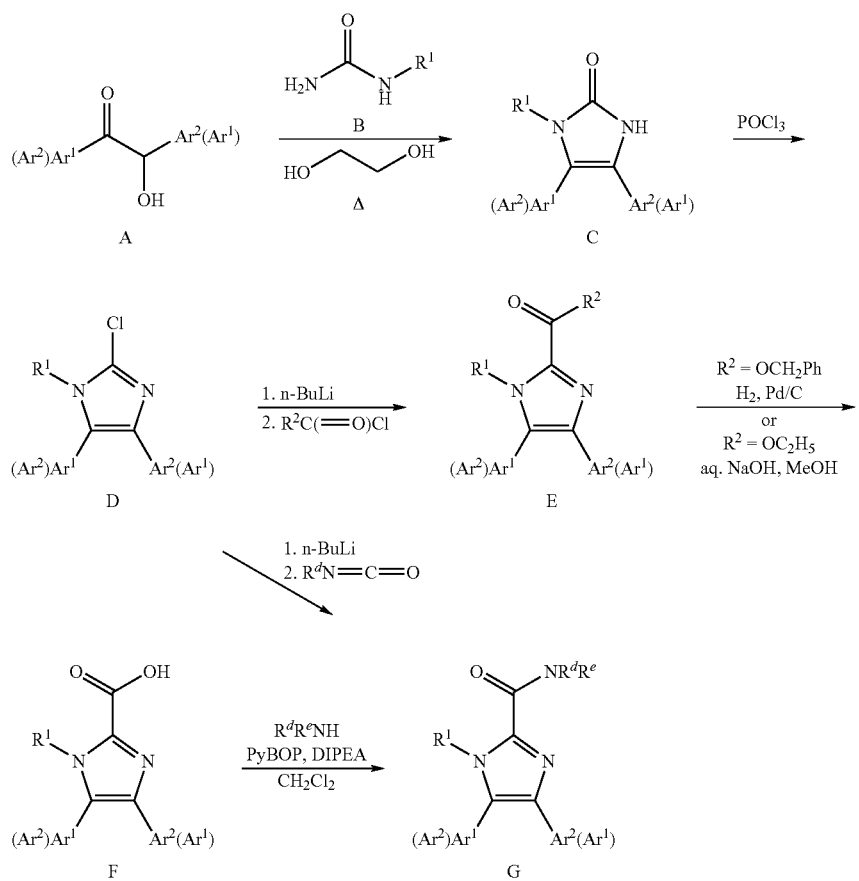

Scheme 1.

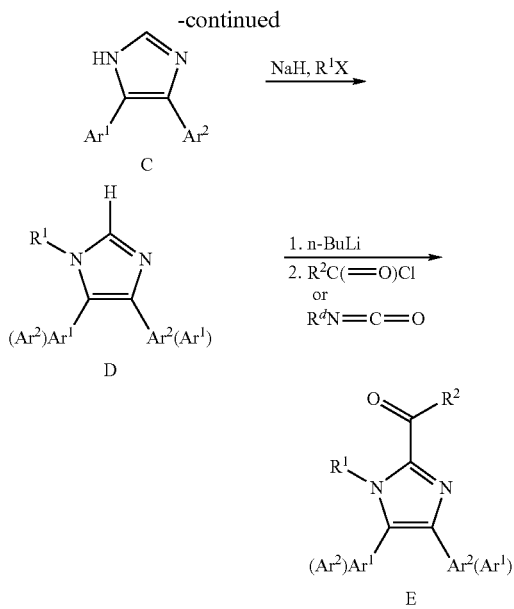

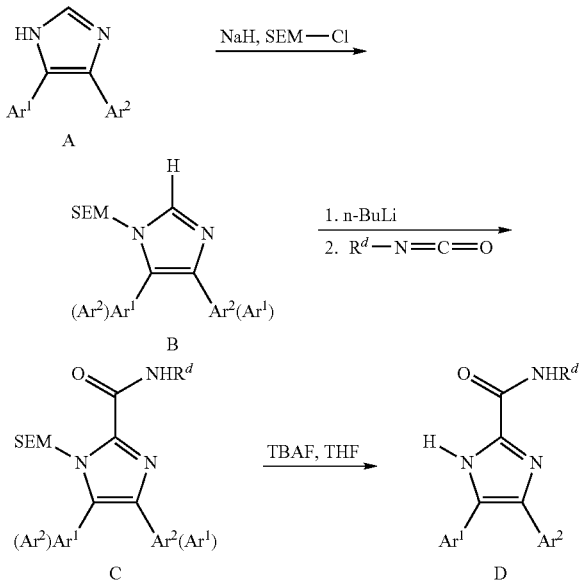

In Scheme 3, the diaryl imidazole A is treated with base (e.g., sodium hydride) followed by alkylation with a suitable protecting group (e.g. 2-trimethylsilyl-ethoxy-methyl chloride, SEM-Cl) to yield N-protected imidazoles B. Deprotonation with strong base (n-butyllithium) followed by treatment with an isocyanate derivative affords the protected 2-carboxamide C. Removal of the SEM-protecting group with TBAF yields the 4,5-diaryl-imidazole-2-carboxamide D which may be reacted with base and an electrophile (as in Scheme 2, B to C).

Scheme 4 outlines the synthesis of acyloin derivatives that are useful in the preparation of compounds of the present invention. A single aryl aldehyde A ($Ar^1=Ar^2$) or a mixture of aryl aldehydes ($Ar^1 \neq Ar^2$) is reacted with sodium cyanide in ethanol to yield benzoin derivative(s) B which may be used as starting materials as outlined in Schemes 1 or 2.

Scheme 4.

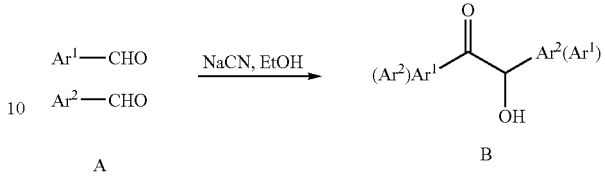

General Procedures.

The HPLC/MS analyses were preformed using a Micromass ZMD mass spectrometer coupled to an Agilent 1100 Series HPLC utilizing a YMC ODS-A 4.6×50 mm column eluting at 2.5 mL/min with a solvent gradient of 10 to 95% B over 4.5 min, then 0.5 min at 95% B: solvent A=0.06% TFA in water; solvent B=0.05% TFA in acetonitrile.

Proton NMR spectra were obtained with a 400 MHz Varian Spectrometer in $CDCl_3$ or $CD_3OD$ and chemical shifts are reported as δ using the deuterium of the solvent as standard and coupling constants are reported in hertz.

EXAMPLE 1

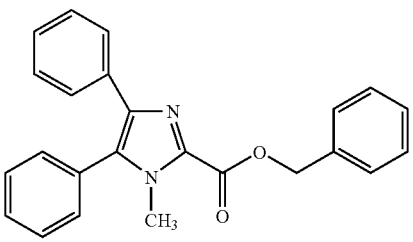

Benzyl 4,5-diphenyl-1-methylimidazole-2-carboxylate

Step A: 4,5-Diphenyl-1-methyl-(1H),(3H)-imidazolin-2-one

A mixture of benzoin (9.5 g, 45 mmol), N-methylurea (10.0 g, 135 mmol) in ethylene glycol (50 mL) was heated to 180° C. for 1.5 hr. The reaction was allowed to cool and was aged for 16 hr before the precipitate was filtered. The solid was recrystallized from ethanol to afford a white solid. The above filtrate was diluted with water and extracted twice with ethyl acetate. The organic layers were washed with brine, dried over sodium sulfate and combined with the above mother liquor to give a crude solid after evaporation. Recrystallization from ethanol afforded a second crop of white solid title compound.

HPLC/MS: 251 (M+1), 292 (100%, M+1+41 ($CH_3CN$)); $R_t$=2.59 min $^1$HNMR ($CD_3OD$): 3.10 (s, 3H), 7.19 (m, 4H), 7.35 (m, 2H), 7.46 (m, 4H).

Step B: 2-Chloro-4,5-diphenyl-1-methylimidazole

A mixture of 4,5-diphenyl-1-methyl-(1H),(3H)-imidazolin-2-one (3.0 g, 12 mmol) from Step A in phosphorous oxychloride (30 mL) was heated to 100° C. for 20 hr. Most of the phosphorous oxychloride was removed in vacuo and the residue was quenched into a mixture of ethyl acetate and saturated aqueous sodium bicarbonate. The layers were separated and the organic layer was washed with brine, dried over sodium sulfate and evaporated. The residue was purified by flash chromatography (2% methylene chloride in 20% ethyl acetate/hexanes) and then crystallized from ethyl acetate/hexanes to afford the title compound. A second crop of slightly impure title compound was obtained from the mother liquors.

HPLC/MS: 269 (M+1); $R_t$=3.23 min; $^1$HNMR (CDCl$_3$): 3.44 (s, 3H), 7.19 (m, 4H), 7.35 (m, 2H), 7.48 (m, 4H).

Step C: Benzyl 4,5-diphenyl-1-methylimidazole-2-carboxylate

A solution of 2-chloro-4,5-diphenyl-1-methylimidazole (1.46 g, 5.4 mmol) from Step B in tetrahydrofuran (THF) (20 mL) under nitrogen was cooled to −70° C. in a dry ice/acetone bath. n-Butyl lithium (1.6 N in hexanes, 10.2 mL, 16.3 mmol) was added via syringe. The reaction was allowed to warm to −20° C. for 2 hr. In a separate round-bottomed flask, a solution of benzyl chloroformate (CBZ-Cl) (4.3 mL, 16.3 mmol) in TBF (10 mL) was cooled to −20° C. The above imidazole reaction was added via a double-tipped needle to the solution of CBZ-Cl and after 20 min the reaction was allowed to warm to rt for 30 min. The reaction was then quenched into an aqueous sodium bicarbonate solution and was then extracted twice with ethyl acetate. The organic layers were washed with brine, dried over sodium sulfate and evaporated. The residue was purified by flash chromatography (5% methylene chloride and 15% ethyl acetate in hexanes) to afford the title compound.

HPLC/MS: 369 (M+1); $R_t$=3.60 min; 1HNMR (CDCl$_3$): 3.81 (s, 3H), 5.49 (s, 2H), 7.20 (m, 4H), 7.35 (m, 2H), 7.40 (m, 2H), 7.50 (m, 5H), 7.56 (m, 2H).

EXAMPLE 2

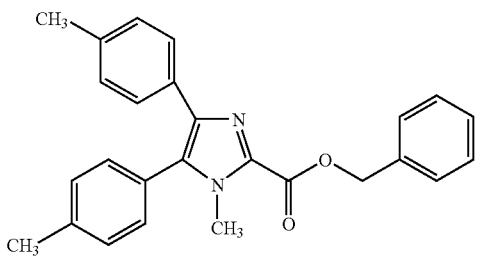

Benzyl 4,5-di-(4-methylphenyl)-1-methylimidazole-2-carboxylate

Step A: 4,5-Di-(4-methylphenyl)-1-methyl-(1H),(3H)-imidazolin-2-one

Using essentially the same procedure as Example 1, Step A, 4,4'-dimethylbenzoin (10.8 g, 45 mmol) was converted to the title compound.

HPLC/MS: 320 (M+1+41 (CH$_3$CN)); $R_t$=3.07 min; $^1$HNMR (CDCl$_3$): 2.29 (s, 3H), 2.43 (s, 3H), 3.15 (s, 3H), 7.03 (d, J=8.2 Hz, 2H), 7.12 (d, J=8.2 Hz, 2H), 7.25 (m, 4H).

Step B: 2-Chloro-4,5-di-(4-methylphenyl)-1-methylimidazole

Using essentially the same procedure as Example 1, Step B, 4,5-di-(4-methylphenyl)-1-methyl-(1H),(3H)-imidazolin-2-one (3.0 g, 10.8 mmol) from Step A was converted to the title compound.

HPLC/MS: 297 (M+1); $R_t$=3.60 min; $^1$HNMR (CDCl$_3$): 2.29 (s, 3H), 2.45 (s, 3H), 3.42 (s, 3H), 7.02 (d, J=8.2 Hz, 2H), 7.22 (d, J=6.3 Hz, 2H), 7.28 (d, J=6.3 Hz, 2H), 7.35 (d, J=8.2 Hz, 2H).

Step C: Benzyl 4,5-di-(4-methylphenyl)-1-methylimidazole-2-carboxylate

Using essentially the same procedure as Example 1, Step C, 2-chloro-4,5-di-(4-methylphenyl)-1-methylimidazoline (1.5 g, 5.1 mmol) from Step B was converted to the title compound.

HPLC/MS: 397 (M+1); $R_t$=3.84 min; 1HNMR (CDCl$_3$): 2.29 (s, 3H), 2.44 (s, 3H), 3.78 (s, 3H), 5.48 (s, 2H), 7.03 (d, 2H), 7.19 (d, 2H), 7.28 (d, 2H), 7.35-7.42 (m, 5H), 7.54 (d, 2H).

EXAMPLE 3

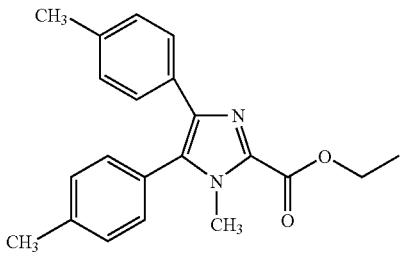

Ethyl 4,5-di-(4-methylphenyl)-1-methylimidazole-2-carboxylate

Using essentially the same procedure as Example 1, Step C, but using ethyl chloroformate, 2-chloro-4,5-di-(4-methylphenyl)-1-methylimidazoline (0.10 g, 0.33 mmol) from Example 2, Step B was converted to the title compound.

HPLC/MS: 335 (M+1); $R_t$=3.31 min; $^1$HNMR (CDCl$_3$): 1.56 (t, 3H), 2.31 (s, 3H), 2.47 (s, 3H), 3.88 (s, 3H), 4.58 (q, 2H), 7.09 (d, 2H), 7.21 (d, 2H), 7.33 (d, 2H), 7.48 (d, 2H).

EXAMPLE 4

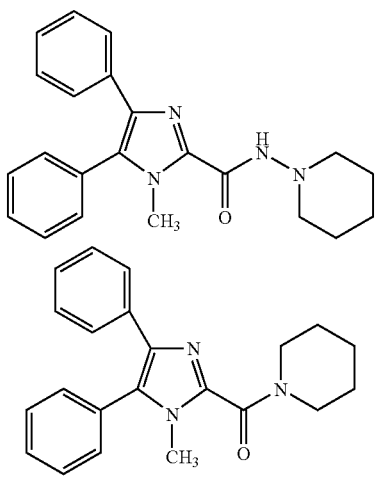

N-(Piperidin-1-yl)-4,5-diphenyl-1-methylimidazole-2-carboxamide and 2-(piperidin-1-ylcarbonyl)-4,5-diphenyl-1-methylimidazole Step A: 4,5-Diphenyl-1-methylimidazole-2-carboxylic acid To a suspension of benzyl 4,5-diphenyl-1-methylimidazole-2-carboxylate (0.43 g, 1.2 mmol) from Example 1, Step C in methanol (10 mL) was added 20% palladium on carbon (50% w/w water, 110 mg) and the mixture was hydrogenated on a Parr shaker at 40 psi for 1 hr. The reaction was filtered and the filtrate was evaporated to dryness to afford the title compound as a white solid. (Note: The title compound readily decarboxylates as the acid.)

HPLC/MS: 279 (M+1); $R_t$=2.05 min.

Step B: N-(Piperidin-1-yl)-4,5-diphenyl-1-methylimidazole-2-carboxamide and 2-(piperidin-1-ylcarbonyl)-4,5-diphenyl-1-methylimidazole A mixture of 4,5-diphenyl-1-methylimidazole-2-carboxylic acid (50 mg, 0.18 mmol) from Step A, 1-aminopiperidine (0.052 mL, 0.36 mmol) (containing a small percent of piperidine as an impurity), PyBOP (NovaChem) (140 mg, 0.2 mmol) and N,N-diisopropyl-N-ethylamine (DIPEA) (0.065 mL, 0.2 mmol) in methylene chloride (2 mL) was stirred at rt for 20 hr. The reaction was diluted with water and extracted twice with methylene chloride. The organic layers were washed with brine, dried over sodium sulfate, and evaporated. The residue was purified twice by prep TLC (1 mm, silica gel) eluting with 5% methylene chloride, 35% ethyl acetate in hexanes to afford the primary product N-(piperidin-1-yl)-4,5-diphenyl-1-methylimidazole-2-carboxamide and 2-(piperidin-1-ylcarbonyl)-4,5-diphenyl-1-methylimidazole as a byproduct.

HPLC/MS: 361 (M+1); $R_t$=2.64 min; $^1$HNMR (CDCl$_3$): 1.4-1.7 (m, 2H), 1.92 (m, 4H), 2.96 (br s, 4H), 3.90 (s, 3H), 7.24 (m, 3H), 7.34 (m, 2H), 7.50 (m, 5H).

and

HPLC/MS: 346 (M+1); $R_t$=2.80 min; $^1$HNMR (CDCl$_3$): 1.75 (m, 6H), 3.64 (s, 3H), 3.78 (m, 2H), 4.03 (m, 2H), 7.21 (m, 3H), 7.38 (m, 2H), 7.49 (m, 5H).

EXAMPLE 5

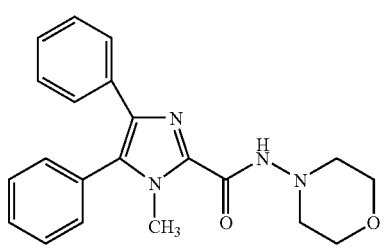

N-(Morpholin-4-yl)-4,5-diphenyl-1-methylimidazole-2-carboxamide

Using essentially the same procedure as Example 4, Step B, but using 4-aminomorpholine (0.025 mL), 4,5-diphenyl-1-methylimidazole-2-carboxylic acid (30 mg, 0.10 mmol) from Example 4, Step A was converted to the title compound.

HPLC/MS: 363 (M+1); $R_t$=2.72 min.

EXAMPLE 6

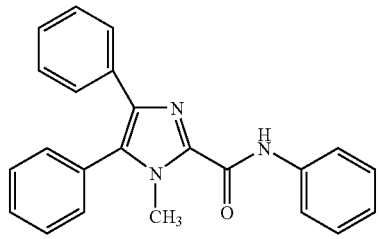

N-Phenyl-4,5-diphenyl-1-methylimidazole-2-carboxamide

Using essentially the same procedure as Example 4, Step B, but using aniline (0.025 mL), 4,5-diphenyl-1-methylimidazole-2-carboxylic acid (30 mg, 0.10 mmol) from Example 4, Step A was converted to the title compound.

HPLC/MS: 354 (M+1); $R_t$=4.31 min.

EXAMPLE 7

N-Hexyl-4,5-diphenyl-1-methylimidazole-2-carboxamide

Using essentially the same procedure as Example 4, Step B, but using n-hexylamine (0.025 mL), 4,5-diphenyl-1-methylimidazole-2-carboxylic acid (30 mg, 0.10 mmol) from Example 4, Step A was converted to the title compound.

HPLC/MS: 362 (M+1); $R_t$=4.24 min.

EXAMPLE 8

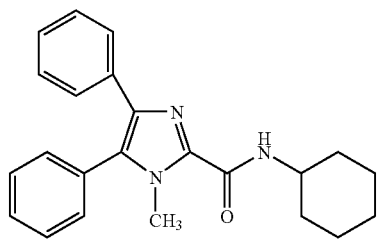

N-Cyclohexyl-4,5-diphenyl-1-methylimidazole-2-carboxamide

Using essentially the same procedure as Example 4, Step B, but using cyclohexylamine (0.025 mL), 4,5-diphenyl-1-methylimidazole-2-carboxylic acid (30 mg, 0.10 mmol) from Example 4, Step A was converted to the title compound.

HPLC/MS: 360 (M+1); $R_t$=3.95 min.

EXAMPLE 9

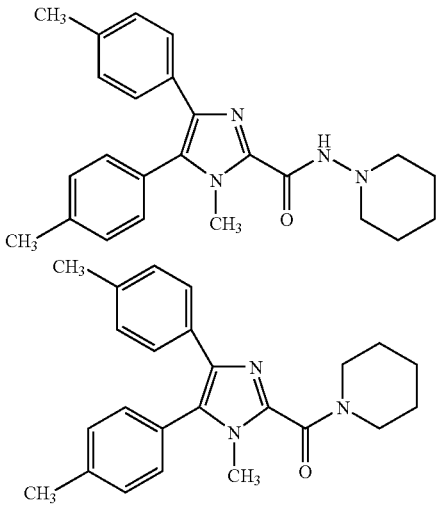

N-(Piperidin-1-yl)-4,5-di-(4-methylphenyl)-1-methylimidazole-2-carboxamide and 2-(piperidin-1-ylcarbonyl)-4,5-di-(4-methylphenyl)-1-methylimidazole Step A: 4,5-Di-(4-methylphenyl)-1-methylimidazole-2-carboxylic acid To a suspension of benzyl 4,5-di-(4-methylphenyl)-1-methylimidazole-2-carboxylate (0.35 g, 0.9 mmol) from Example 2, Step C in methanol (10 mL) was added 20% palladium on carbon (50% w/w water, 100 mg) and the mixture was hydrogenated at 40 psi for 1 hr. The reaction was filtered and the filtrate was evaporated to dryness to afford the title compound as a white solid. (Note: The title compound readily decarboxylates as the acid.)

HPLC/MS: 307 (M+1); $R_t$=2.48 min.

Step B: N-(Piperidin-1-yl)-4,5-di-(4-methylphenyl)-1-methylimidazole-2-carboxamide and 2-(piperidin-1-ylcarbonyl)-4,5-di-(4-methylphenyl)-1-methylimidazole A mixture of 4,5-di-(4-methylphenyl)-1-methylimidazole-2-carboxylic acid (25 mg, 0.08 mmol) from Step A, 1-aminopiperidine (0.020 mL, 0.16 mmol) (containing a small percent of piperidine as an impurity), PyBOP (NovaChem) (65 mg, 0.1 mmol) and DIPEA (0.025 mL, 0.1 mmol) in methylene chloride (1 mL) was stirred at rt for 20 hr. The reaction was diluted with water and extracted twice with methylene chloride. The organic layers were washed with brine, dried over sodium sulfate, and evaporated. The residue was purified twice by prep TLC (1 mm, silica gel) eluting with 5% methylene chloride, 35% ethyl acetate in hexanes to afford the primary product N-(piperidin-1-yl)-4,5-di-(4-methylphenyl)-1-methylimidazole-2-carboxamide (10 mg, 32%) and 2-(piperidin-1-ylcarbonyl)-4,5-di-(4-methylphenyl)-1-methylimidazole as a byproduct.

HPLC/MS: 389 (M+1); $R_t$=3.04 min and

HPLC/MS: 374 (M+1); $R_t$=3.12 min

EXAMPLE 10

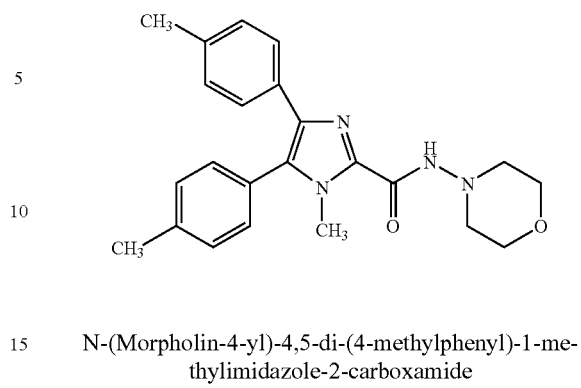

N-(Morpholin-4-yl)-4,5-di-(4-methylphenyl)-1-methylimidazole-2-carboxamide

Using essentially the same procedure as Example 9, Step B, but using 4-aminomorpholine (0.025 mL), 4,5-di-(4-methylphenyl)-1-methylimidazole-2-carboxylic acid (25 mg, 0.08 mmol) from Example 9, Step A was converted to the title compound.

HPLC/MS: 391 (M+1); $R_t$=3.12 min.

EXAMPLE 11

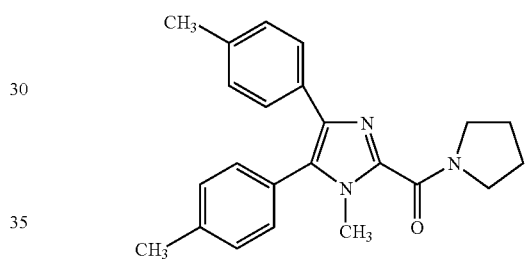

2-(Pyrrolidin-1-ylcarbonyl)-4,5-di-(4-methylphenyl)-1-methylimidazole

Using essentially the same procedure as Example 9, Step B, but using pyrrolidine (0.022 mL), 4,5-di-(4-methylphenyl)-1-methylimidazole-2-carboxylic acid (25 mg, 0.08 mmol) from Example 9, Step A was converted to the title compound.

HPLC/MS: 360 (M+1); $R_t$=3.12 min.

EXAMPLE 12

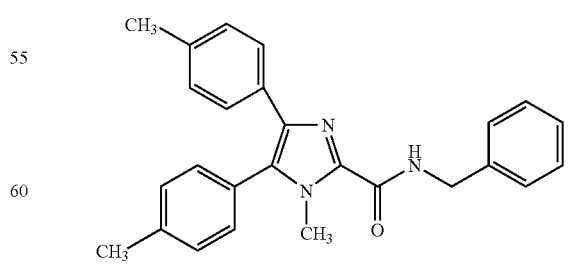

N-Benzyl-4,5-di-(4-methylphenyl)-1-methylimidazole-2-carboxamide

Using essentially the same procedure as Example 9, Step B, but using benzylamine (0.022 mL), 4,5-di-(4-methylphenyl)-1-methylimidazole-2-carboxylic acid (25 mg, 0.08 mmol) from Example 9, Step A was converted to the title compound.

HPLC/MS: 396 (M+1); $R_t$=4.13 min.

EXAMPLE 13

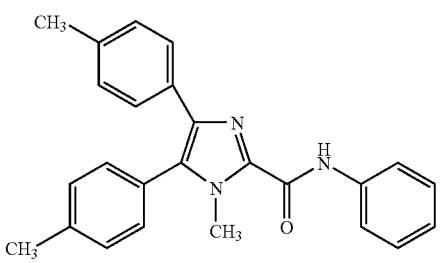

N-Phenyl-4,5-di-(4-methylphenyl)-1-methylimidazole-2-carboxamide

Using essentially the same procedure as Example 9, Step B, but using aniline (0.020 mL), 4,5-di-(4-methylphenyl)-1-methylimidazole-2-carboxylic acid (25 mg, 0.08 mmol) from Example 9, Step A was converted to the title compound.

HPLC/MS: 382 (M+1); $R_t$=4.43 min.

EXAMPLE 14

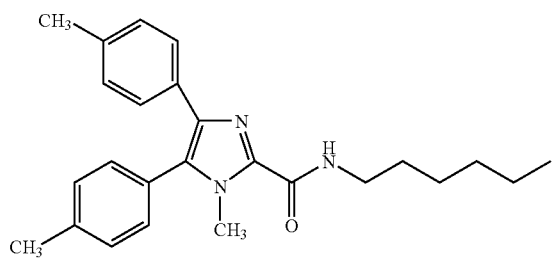

N-Hexyl-4,5-di-(4-methylphenyl)-1-methylimidazole-2-carboxamide

Using essentially the same procedure as Example 9, Step B, but using hexylamine (0.020 mL), 4,5-di-(4-methylphenyl)-1-methylimidazole-2-carboxylic acid (25 mg, 0.08 mmol) from Example 9, Step A was converted to the title compound.

HPLC/MS: 390 (M+1); $R_t$=4.45 min.

EXAMPLE 15

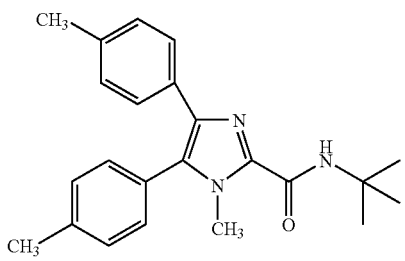

N-t-Butyl-4,5-di-(4-methylphenyl)-1-methylimidazole-2-carboxamide

Using essentially the same procedure as Example 9, Step B, but using t-butylamine (0.022 mL), 4,5-di-(4-methylphenyl)-1-methylimidazole-2-carboxylic acid (25 mg, 0.08 mmol) from Example 9, Step A was converted to the title compound.

HPLC/MS: 362 (M+1); $R_t$=3.92 min.

EXAMPLE 16

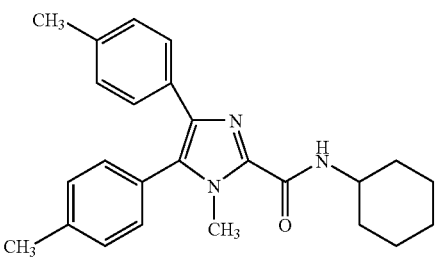

N-Cyclohexyl-4,5-di-(4-methylphenyl)-1-methylimidazole-2-carboxamide

Using essentially the same procedure as Example 9, Step B, but using cyclohexylamine (0.020 mL), 4,5-di-(4-methylphenyl)-1-methylimidazole-2-carboxylic acid (25 mg, 0.08 mmol) from Example 9, Step A was converted to the title compound.

HPLC/MS: 388 (M+1); $R_t$=4.19 min.

EXAMPLE 17

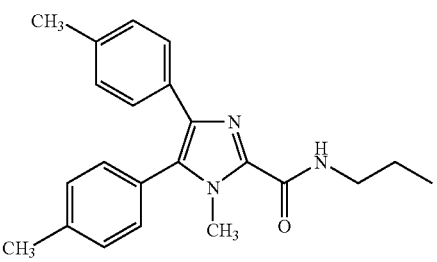

N-Propyl-4,5-di-(4-methylphenyl)-1-methylimidazole-2-carboxamide

Using essentially the same procedure as Example 9, Step B, but using n-propylamine (0.015 mL), 4,5-di-(4-methylphenyl)-1-methylimidazole-2-carboxylic acid (25 mg, 0.08 mmol) from Example 9, Step A was converted to the title compound.

HPLC/MS: 348 (M+1); $R_t$=3.76 min.

EXAMPLE 18

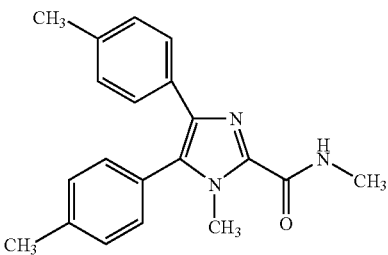

N-Methyl-4,5-di-(4-methylphenyl)-1-methylimidazole-2-carboxamide

Using essentially the same procedure as Example 9, Step B, but using methylamine (0.20 mL of 2N methylamine in THF), 4,5-di-(4-methylphenyl)-1-methylimidazole-2-carboxylic acid (25 mg, 0.08 mmol) from Example 9, Step A was converted to the title compound.

HPLC/MS: 320 (M+1); $R_t$=3.28 min.

EXAMPLE 19

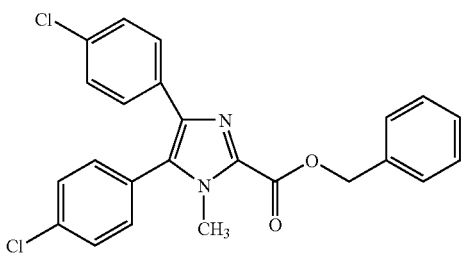

Benzyl 4,5-di-(4-chlorophenyl)-1-methylimidazole-2-carboxylate

Step A: 4,5-Di-(4-chlorophenyl)imidazole

A mixture of 4,4'-dichlorobenzil (3.0 gm, 10.8 mmol) and paraformaldehyde (2.0 gm, 67 mmol) in formamide (50 mL) was heated to 220° C. for 2.5 hr. The reaction was cooled, diluted with water, and extracted twice with ethyl acetate. The organic layers were washed with brine, dried over sodium sulfate, and evaporated. The residue was crystallized from isopropyl acetate (or ethyl acetate) to provide the title compound as a white solid in 3 crops.

HPLC/MS: 289 (M+1), 291 (M+3); $R_t$=2.64 min.

Step B: 4,5-Di-(4-chlorophenyl)-1-methylimidazole

To a solution of 4,5-di-(4-chlorophenyl)imidazole (300 mg, 1.0 mmol) from Step A and methyl iodide (0.10 mL, 2.0 mmol) in DMF (5 mL) was added sodium hydride (80 mg 60% in mineral oil, 1.5 mmol) all at once at rt. After stirring for 1 hr, the reaction was quenched into water and extracted twice with ethyl acetate. The organic layers were washed with brine, dried over sodium sulfate, and evaporated. The residue was purified by flash chromatography (10% methylene chloride, 30% ethyl acetate in hexanes) to provide the title compound as a white solid.

HPLC/MS: 303 (M+1), 305 (M+3); $R_t$=2.53 min; $^1$HNMR (CDCl$_3$): 3.60 (s, 3H), 7.25 (d, J=8.5 Hz, 2H), 7.29 (d, J=8.5 Hz, 2H), 7.44 (d, J=8.5 Hz, 2H), 7.50 (d, J=8.5 Hz, 2H), 8.08 (br s, 1H).

Step C: Benzyl 4,5-di-(4-chlorophenyl)-1-methylimidazole-2-carboxylate

To a solution of 4,5-di-(4-chlorophenyl)-1-methylimidazole (0.25 gm, 0.825 mmol) from Step B in THF (5 mL) cooled to −70° C. in a dry ice/acetone bath was added via syringe n-butyl lithium (1.6 N in hexanes, 0.62 mL, 1.0 mmol). The reaction was stirred at −70° C. for 30 min and then a solution of CBZ-Cl (0.42 mL, 1.65 mmol) in THF (2 mL) was added rapidly. The reaction was warmed to rt over 1 hr. The reaction was poured into an aq. sodium bicarbonate solution and then extracted twice with ethyl acetate. The organic layers were washed with brine, dried over sodium sulfate, and evaporated. The residue was purified by flash chromatography (15% ethyl acetate in hexanes) to provide the title compound as a white solid.

HPLC/MS: 437 (M+1), 439 (M+3); $R_t$=4.37 min.

EXAMPLE 20

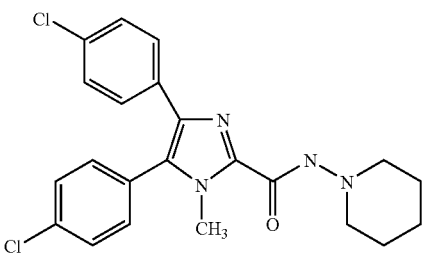

-continued

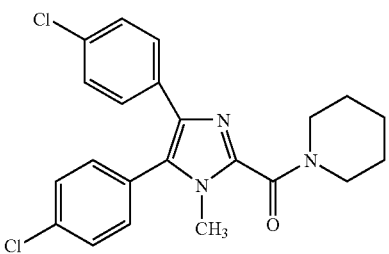

N-(Piperidin-1-yl)-4,5-di-(4-chlorophenyl)-1-methylimidazole-2-carboxamide and 2-(piperidin-1-ylcarbonyl)-4,5-di-(4-chlorophenyl)-1-methylimidazole Step A: 4,5-Di-(4-chlorophenyl)-1-methylimidazole-2-carboxylic acid To a suspension of benzyl 4,5-di-(4-chlorophenyl)-1-methylimidazole-2-carboxylate (185 mg, 0.42 mmol) from Example 19, Step C in methanol (20 mL) was added aq. 5N sodium hydroxide (0.25 mL, 1.27 mmol). The reaction was stirred at rt for 20 hr, concentrated in vacuo, acidified with 2N hydrochloric acid (0.50 mL), and extracted twice with ethyl acetate. The organic layers were washed with brine, dried over sodium sulfate, and evaporated to dryness to afford the crude title acid (150 mg) as a mixture with decarboxylated material. This material was used directly in Step B.

HPLC/MS: 347 (M+1), 349 (M+3); $R_t$=2.72 min.

Step B: N-(Piperidin-1-yl)-4,5-di-(4-chlorophenyl)-1-methylimidazole-2-carboxamide and 2-(piperidin-1-ylcarbonyl)-4,5-di-(4-chlorophenyl)-1-methylimidazole A mixture of crude 4,5-di-(4-chlorophenyl)-1-methylimidazole-2-carboxylic acid (45 mg, 0.13 mmol) from Step A (<50% pure due to decarboxylation), 1-aminopiperidine (0.050 mL, 0.33 mmol) (containing a small percent of piperidine as an impurity), Py-BOP (NovaChem) (110 mg, 0.16 mmol) and DIPEA (0.060 mL, 0.16 mmol) in methylene chloride (2 mL) was stirred at rt for 20 hr. The reaction was diluted with water and extracted twice with methylene chloride. The organic layers were washed with brine, dried over sodium sulfate, and evaporated. The residue was purified twice by prep TLC (1 mm, silica gel) eluting with 40% ethyl acetate in hexanes to afford the primary product N-piperidin-1-yl-4,5-di-(4-chlorophenyl)-1-methylimidazole-2-carboxamide as the lower Rf product and 2-(piperidin-1-ylcarbonyl)-4,5-di-(4-chlorophenyl)-1-methylimidazole as a higher Rf byproduct along with recovered 4,5-di-(4-chlorophenyl)imidazole.

HPLC/MS: 429 (M+1), 431 (M+3); $R_t$=3.55 min and
HPLC/MS: 414 (M+1), 415 (M+3); $R_t$=3.79 min

EXAMPLE 21

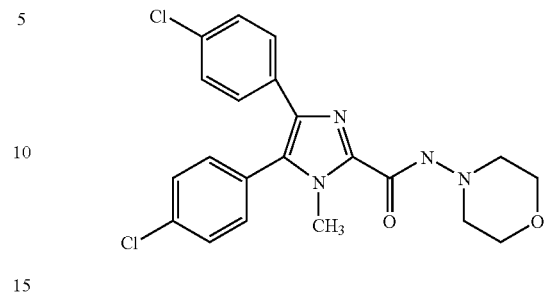

N-(Morpholin-1-yl)-4,5-di-(4-chlorophenyl)-1-methylimidazole-2-carboxamide

Using essentially the same procedure as Example 20, Step B, but using 4-aminomorpholine (0.020 mL, 0.12 mmol), 4,5-di-(4-chlorophenyl)-1-methylimidazole-2-carboxylic acid (20 mg, 0.060 mmol) from Example 20, Step A was converted to the title compound.

HPLC/MS: 431 (M+1), 433 (M+3); $R_t$=3.55 min.

EXAMPLE 22

N-(Hexyl)-4,5-di-(4-chlorophenyl)-1-methylimidazole-2-carboxamide

Using essentially the same procedure as Example 20, Step B, but using hexylamine (0.020 mL, 0.12 mmol), 4,5-di-(4-chlorophenyl)-1-methylimidazole-2-carboxylic acid (20 mg, 0.060 mmol) from Example 20, Step A was converted to the title compound.

HPLC/MS: 430 (M+1), 432 (M+3); $R_t$=4.91 min.

EXAMPLE 23

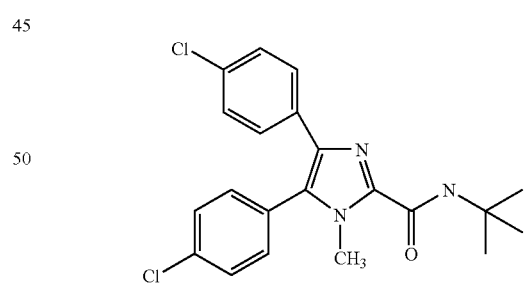

N-(t-Butyl)-4,5-di-(4-chlorophenyl)-1-methylimidazole-2-carboxamide

Using essentially the same procedure as Example 20, Step B, but using t-butylamine (0.020 mL, 0.12 mmol), 4,5-di-(4-chlorophenyl)-1-methylimidazole-2-carboxylic acid (20 mg, 0.060 mmol) from Example 20, Step A was converted to the title compound.

HPLC/MS: 402 (M+1), 404 (M+3); $R_t$=4.53 min.

EXAMPLE 24

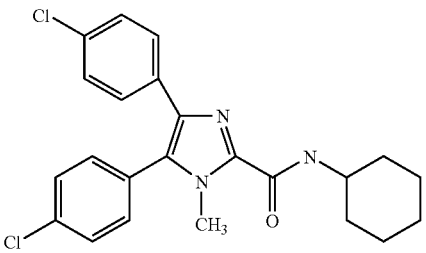

N-(Cyclohexyl)-4,5-di-(4-chlorophenyl)-1-methylimidazole-2-carboxamide

Using essentially the same procedure as Example 20, Step B, but using cyclohexylamine (0.020 mL, 0.12 mmol), 4,5-di-(4-chlorophenyl)-1-methylimidazole-2-carboxylic acid (20 mg, 0.060 mmol) from Example 20, Step A was converted to the title compound.

HPLC/MS: 428 (M+1), 430 (M+3); $R_t$=4.53 min.

EXAMPLE 25

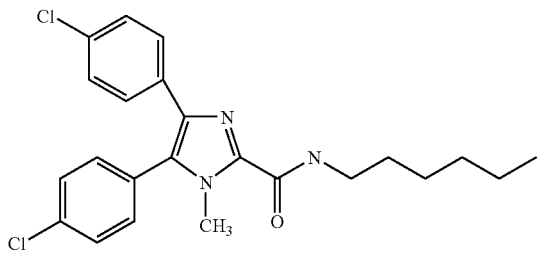

N-Hexyl-4,5-di-(4-chlorophenyl)imidazole-2-carboxamide

Step A: 4,5-Di-(4-chlorophenyl)-1-(2-(trimethylsilyl)ethoxymethyl)imidazole

To a solution of 4,5-di-(4-chlorophenyl)imidazole (500 mg, 1.7 mmol) from Example 20, Step A and 2-(trimethylsilyl)ethoxymethyl chloride (SEM-Cl) (0.46 mL, 2.6 mmol) in DMF (8 mL) at rt was added sodium hydride (60% in mineral oil) (135 mg, 3.4 mmol). The reaction was stirred for 20 min, poured into an aq. bicarbonate solution, and extracted twice with ethyl acetate. The organic layers were washed with brine, dried over sodium sulfate, and evaporated. The residue was purified by flash chromatography (25% ethyl acetate in hexanes) to afford the title compound as an oil.

HPLC/MS: 419 (M+1), 421 (M+3); $R_t$=3.60 min.

Step B: N-Hexyl-4,5-di-(4-chlorophenyl)-1-(2-(trimethylsilyl)ethoxymethyl)imidazole-2-carboxylate A solution of 4,5-di-(4-chlorophenyl)-1-(2-(trimethylsilyl)ethoxymethyl)imidazole (40 mg, 0.10 mmol) from Step A in THF (1 mL) was cooled to −70° C. in a dry ice/acetone bath and n-butyl lithium (1.6M in hexanes, 0.075 mL, 0.12 mmol) was added. After 1 hr, hexyl isocyanate (0.030 mL, 0.20 mmol) was added and the reaction was warmed to rt for 1 hr. The reaction was quenched into an aq. sodium bicarbonate solution and extracted twice with ethyl acetate. The organic layers were washed with brine, dried over sodium sulfate, and evaporated. The residue was purified by prep TLC (1 mm, silica) (25% ethyl acetate in hexanes) to afford the title compound as an oil (12.5 mg, 24%) along with recovered starting material (23 mg, 57%).

HPLC/MS: 546 (M+1), 548 (M+3); $R_t$=3.89 min.

Step C: N-Hexyl-4,5-di-(4-chlorophenyl)imidazole-2-carboxylate

A solution of N-hexyl-4,5-di-(4-chlorophenyl)-1-(2-(trimethylsilyl)ethoxymethyl)imidazole-2-carboxylate (12.5 mg, 0.023 mmol) from Step B and tetrabutylammonium fluoride (TBAF) (1N in THF, 0.15 mL, 0.15 mmol) in THF (2 mL) was stirred at rt for 24 hr. Additional TBAF (0.10 mL) was added and the reaction was stirred another 72 hr. The volatiles were evaporated under nitrogen and the residue was purified by prep TLC (0.5 mm, silica) (15% ethyl acetate in hexanes) to afford the title compound.

HPLC/MS: 416 (M+1), 418 (M+3); $R_t$=2.64 min.

EXAMPLE 26

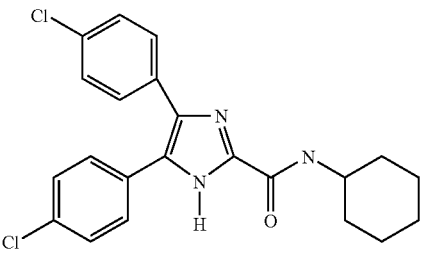

N-Cyclohexyl-4,5-di-(4-chlorophenyl)imidazole-2-carboxamide

Using essentially the same procedure as Example 25, Step B-C, but using cyclohexyl isocyanate (0.027 mL, 0.21 mmol) in Step B, 4,5-di-(4-chlorophenyl)-1-(2-(trimethylsilyl)ethoxymethyl)imidazole (36 mg, 0.086 mmol) from Example 25, Step A was converted to the SEM intermediate and then to the title compound with TBAF.

HPLC/MS: 414 (M+1), 416 (M+3); $R_t$=3.55 min.

EXAMPLE 27

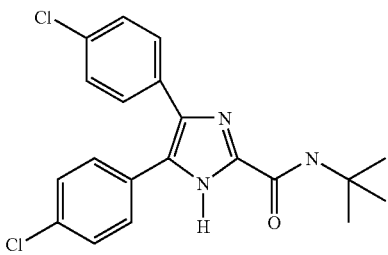

N-t-Butyl-4,5-di-(4-chlorophenyl)imidazole-2-carboxamide

Using essentially the same procedure as Example 25, Step B-C, but using t-butyl isocyanate (0.016 mL, 0.14 mmol) in Step B, 4,5-di-(4-chlorophenyl)-1-(2-(trimethylsilyl) ethoxymethyl)imidazole (23 mg, 0.055 mmol) from Example 25, Step A was converted to the SEM intermediate and then to the title compound with TBAF.

HPLC/MS: 388 (M+1), 390 (M+3); $R_t$=2.45 min.

EXAMPLE 28

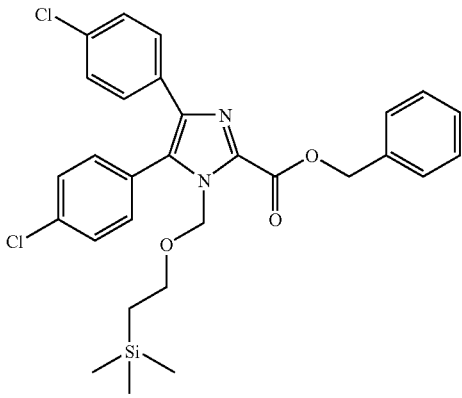

Benzyl 4,5-di-(4-chlorophenyl)-1-(2-(trimethylsilyl) ethoxymethyl)imidazole-2-carboxylate Using essentially the same procedure as Example 25, Step B, but using CBZ-Cl (0.030 mL, 1.2 mmol) in Step B, 4,5-di-(4-chlorophenyl)-1-(2-(trimethylsilyl)ethoxymethyl)imidazole (31 mg, 0.074 mmol) from Example 25, Step A was converted to the title compound.

HPLC/MS: 553 (M+1), 555 (M+3); $R_t$=5.2 min.

EXAMPLE 29

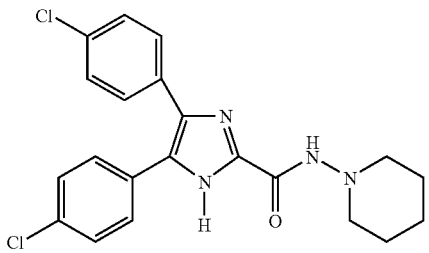

N-(Piperidin-1-yl)-4,5-di-(4-chlorophenyl)imidazole-2-carboxamide

Using essentially the same procedure as Example 20, benzyl 4,5-di-(4-chlorophenyl)-1-(2-(trimethylsilyl)ethoxymethyl)imidazole (19 mg, 0.034 mmol) from Example 28, was converted to the SEM intermediate amide and then to the title compound with TBAF as in Example 25, Step C.

HPLC/MS: 415 (M+1), 417 (M+3); $R_t$=3.41 min.

EXAMPLE 30

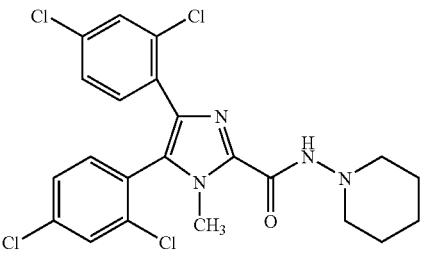

N-(Piperidin-1-yl)-4,5-di-(2,4-dichlorophenyl)-1-methylimidazole-2-carboxamide

Step A: (+/−)-2,2',4,4'-Tetrachlorobenzoin

To a mixture of 2,4-dichlorobenzaldehyde (5.0 gm, 29 mmol) in ethanol (10 mL) was added a solution of sodium cyanide (500 mg, 10 mmol) in water (5 mL). The reaction was heated to reflux (100-110° C.) for 1 hr and was then cooled, diluted with water, and extracted twice with ethyl acetate. The organic layers were washed with brine, dried over sodium sulfate, and evaporated. The residue was purified by flash chromatography (10% methylene chloride, 10% ethyl acetate in hexanes) to afford the title compound as an oil.

HPLC/MS: no parent ion, 372 (M+1−18 (H$_2$O)+41 (CH$_3$CN)), 374 (100%, M+3−18 (H$_2$O)+41 (CH$_3$CN)), 376 (M+5−18 (H$_2$O)+41 (CH$_3$CN)); $R_t$=3.8 min $^1$HNMR (CDCl$_3$): 4.36 (d, 1H), 6.27 (d, 1H), 7.25 (s, 4H), 7.32 (br s, 1H), 7.41 (br s, 1H).

Step B: 4,5-Di-(2,4-dichlorophenyl)imidazole

A mixture of (+/−)-2,2',4,4'-tetrachlorobenzoin (1.0 gm, 2.9 mmol) from Step A and paraformaldehyde (0.70 gm, 24 mmol) in formamide (20 mL) was heated to 200-210° C. for 3 hr. The reaction was cooled to rt, diluted with water, and extracted twice with ethyl acetate. The organic layers were washed with brine, dried over sodium sulfate, and evaporated. The residue was purified by flash chromatography, eluting first with 10% ethyl acetate in hexanes to afford 4,5-di-(2,4-dichlorophenyl)oxazole as a higher Rf byproduct and then with 75% ethyl acetate in hexanes to elute the title compound as an oil.

HPLC/MS: 357 (M+1), 359 (100%, M+3), 361 (M+5); $R_t$=2.72 min.

Step C: 4,5-Di-(2,4-dichlorophenyl)-1-methylimidazole

To a solution of 4,5-di-(2,4-dichlorophenyl)imidazole (230 mg, 0.65 mmol) from Step B and methyl iodide (0.062 mL, 1.0 mmol) in DMF (5 mL) was added sodium hydride (60% in mineral oil, 52 mg, 1.3 mmol). The reaction was stirred at rt for 3 hr and was then quenched with aq. sodium bicarbonate and extracted twice with ethyl acetate. The organic layers were washed with brine, dried over sodium sulfate, and evaporated. The residue was purified by flash chromatography (50% ethyl acetate in hexanes) to afford the title compound.

HPLC/MS: 371 (M+1), 373 (100%, M+3), 375 (M+5); $R_t$=2.85 min.

Step D: Ethyl 4,5-di-(2,4-dichlorophenyl)-1-methylimidazole-2-carboxylate

To a solution of 4,5-di-(2,4-dichlorophenyl)-1-methylimidazole (200 mg, 0.54 mmol) from Step C in THF (5 mL) cooled to −70° C. in a dry ice/acetone bath was added 1.6N n-butyl lithium in hexanes (0.40 mL, 0.65 mmol). The reaction was stirred for 1 hr and then ethyl chloroformate (0.10 mL, 1.1 mmol) was added via syringe. The reaction was allowed to warm to rt for 1 hr and was then quenched with aq. sodium bicarbonate and extracted twice with ethyl acetate. The organic layers were washed with brine, dried over sodium sulfate, and evaporated. The residue was purified by Prep TLC (2×1 mm, silica) (25% ethyl acetate in hexanes) to afford the title compound.

HPLC/MS: 497 (M+1), 499 (100%, M+3), 501 (M+5); $R_t$=3.95 min.

Step E: N-(Piperidin-1-yl)-4,5-di-(2,4-dichlorophenyl)-1-methylimidazole-2-carboxamide A mixture of ethyl 4,5-di-(2,4-dichlorophenyl)-1-methylimidazole-2-carboxylate (20 mg, 0.045 mmol) from Step D in neat 1-aminopiperidine (1 mL) was heated at 90° C. for 72 hr. Most of the amine was evaporated under a stream of nitrogen and the residue was purified by Prep TLC (1 mm, silica) (25% ethyl acetate in hexanes to afford the title compound.

HPLC/MS: 497 (M+1), 499 (100%, M+3), 501 (M+5); $R_t$=3.95 min.

EXAMPLE 31

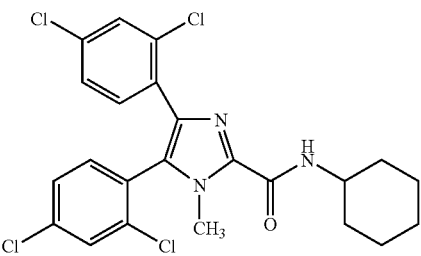

N-(Cyclohexyl)-4,5-di-(2,4-dichlorophenyl)-1-methylimidazole-2-carboxamide

Using essentially the same procedure as Example 30, Step E, but using cyclohexylamine (1 mL), ethyl 4,5-di-(2,4-dichlorophenyl)-1-methylimidazole-2-carboxylate (10 mg, 0.022 mmol) from Example 30, Step D was converted to the title compound.

HPLC/MS: 496 (M+1), 498 (100%, M+3), 500 (M+5); $R_t$=5.04 min.

EXAMPLE 32

N-(Piperidin-1-yl)-4-(4-chlorophenyl)-5-(2,4-dichlorophenyl)-1-methylimidazole-2-carboxamide Step A: (+/−)-4'-Chloro-2-hydroxy-2-(2,4-dichlorophenyl)acetophenone (Higher Rf Isomer) and (+/−)-2',4'-dichloro-2-hydroxy-2-(4-chlorophenyl)acetophenone (Lower Rf Isomer)

To a mixture of 2,4-dichlorobenzaldehyde (5.3 gm, 30 mmol) and 4-chlorobenzaldehyde (10 gm, 70 mmol) in ethanol (30 mL) was added a solution of sodium cyanide (1.0 mg, 20 mmol) in water (10 mL). The reaction was heated to reflux (100-110° C.) for 5 hr and was then cooled, diluted with water, and extracted twice with ethyl acetate. The organic layers were washed with brine, dried over sodium sulfate, and evaporated. The residue was purified by flash chromatography (10% methylene chloride, 5-10% ethyl acetate in hexanes) to afford first recovered aldehydes and then the higher Rf isomeric trichloro product (contaminated with<10% of (+/−)-2,2',4,4'-tetrachlorobenzoin having the same Rf). This was crystallized from ethyl acetate/hexanes to afford pure (+/−)-4'-chloro-2-hydroxy-2-(2,4-dichlorophenyl)acetophenone.

HPLC/MS: no parent ion; 297 (M+1-18 ($H_2O$)), 299 (100%, M+3-18 ($H_2O$)); 338 (100%, M+1-18 ($H_2O$)+41 ($CH_3CN$)), 340 (M+3-18 ($H_2O$)+41 ($CH_3CN$)); $R_t$=3.6 min $^1$HNMR ($CDCl_3$): 4.45 (d, J=4 Hz, 1H), 6.28 (br d, 1H), 7.05 (d, J=8.4 Hz, 1H), 7.19 (dd, J=2.2 and 8.4 Hz, 1H), 7.41 (dt, J=2.5 and 8.5 Hz, 2H), 7.46 (d, J=2.2 Hz, 1H), 7.85 (dt, J=2.5 and 8.5 Hz).

Further elution (10% methylene chloride, 25% ethyl acetate in hexanes) gave a mixture of the lower Rf isomeric trichloro product and (+/−)-4,4'-dichlorobenzoin. This was crystallized from ethyl acetate/hexanes to afford pure (+/−)-4,4'-dichlorobenzoin (1.5 gm). The mother liquor was concentrated to give impure (+/−)-2',4'-dichloro-2-hydroxy-2-(4-chlorophenyl)acetophenone as an oil.

HPLC/MS: no parent ion; $R_t$=3.6 min $^1$HNMR ($CDCl_3$): 4.55 (br s, 1H), 5.81 (s, 1H), 7.26 (dt, J=2.5 and 8.5 Hz, 2H), 7.32 (dt, J=2.5 and 8.5 Hz, 2H), 7.39 (dd, J=2.0 and 8.4 Hz, 1H), 7.48 (d, J=2.0 Hz, 1H), 7.67 (d, J=8.4 Hz) and impurities.

Step B: 4-(4-Chlorophenyl)-5-(2,4-dichlorophenyl)imidazole

A mixture of (+/−)-4'-chloro-2-hydroxy-2-(2,4-dichlorophenyl)acetophenone (4.0 gm, 13 mmol) (higher Rf isomer from Step A) and paraformaldehyde (4.0 gm, 130 mmol) in formamide (60 mL) was heated to 200-210° C. for 3 hr. The reaction was cooled to rt, diluted with water, and extracted twice with ethyl acetate. The organic layers were washed with brine, dried over sodium sulfate, and evaporated. The residue was purified by flash chromatography, eluting first with 10% methylene chloride, 10% ethyl acetate in hexanes to afford a mixture of isomeric oxazoles as higher Rf byproducts (1.7 gm, 40%) (HPLC/MS: 324 (M+1), 326 (M+3); $R_t$=4.3 min). Further elution with 50-100% ethyl acetate in hexanes gave the title imidazole product. This was crystallized from ethyl acetate/hexanes to afford the title compound as a white solid.

HPLC/MS: 323 (M+1), 325 (M+3); $R_t$=2.6 min

Similar reaction of the impure lower Rf isomeric (+/−)-2',4'-dichloro-2-hydroxy-2-(4-chlorophenyl)acetophenone afforded a mixture which could be separated by flash chromatography to give the same isomeric oxazoles, then additional title imidazole, and then (+/−)-4,5-(4-chlorophenyl) imidazole.

Step C: 4-(4-Chlorophenyl)-5-(2,4-dichlorophenyl)-1-methylimidazole (Higher Rf Isomer) and 4-(2,4-dichlorophenyl)-5-(4-chlorophenyl)-1-methylimidazole (Lower Rf Isomer)

To a solution of 4-(4-chlorophenyl)-5-(2,4-dichlorophenyl)imidazole (550 mg, 1.7 mmol) from Step B and methyl iodide (0.16 mL, 2.5 mmol) in DMF (10 mL) was added sodium hydride (60% in mineral oil, 140 mg, 3.4 mmol). The reaction was stirred at rt for 1 hr and was then quenched with aq. sodium bicarbonate and extracted twice with ethyl acetate. The organic layers were washed with brine, dried over sodium sulfate, and evaporated. The residue was purified by flash chromatography (50-75% ethyl acetate in hexanes) to afford the title higher Rf compound.

HPLC/MS: 337 (M+1), 339 (M+3); $R_t$=2.7 min.; $^1$HNMR ($CDCl_3$): 3.48 (s, 3H), 7.22 (dt, J=2.0 and 8.6 Hz, 2H), 7.26 (d, J=8.2 Hz, 1H), 7.37 (dt, J=2.0 and 8.6 Hz, 2H), 7.38 (dd, J=2.2 and 8.2 Hz, 1H), 7.63 (d, J=2.2 Hz, 1H), 7.74 (s, 1H).

Further elution with 100% ethyl acetate afforded a mixture of isomers which were further separated by Prep TLC (3×1 mm, silica) (100% ethyl acetate) to give additional higher Rf isomer and pure lower Rf isomer.

HPLC/MS: 337 (M+1), 339 (M+3); $R_t$=2.7 min; $^1$HNMR (CDCl$_3$): 3.67 (s, 3H), 7.12 (dt, J=2.0 and 8.6 Hz, 2H), 7.20 (dd, J=2.0 and 8.2 Hz, 1H), 7.29 (d, J=8.2 Hz, 1H), 7.36 (dt, J=2.0 and 8.6 Hz, 2H), 7.37 (d, J=2.0 Hz, 1H), 7.78 (s, 1H).

Step D: Ethyl 4-(4-chlorophenyl)-5-(2,4-dichlorophenyl)-1-methylimidazole-2-carboxylate To a solution of 4-(4-chlorophenyl)-5-(2,4-dichlorophenyl)-1-methylimidazole (100 mg, 0.30 mmol) from Step C in THF (4 mL) cooled to −70° C. in a dry ice/acetone bath was added 1.6N n-butyl lithium in hexanes (0.22 mL, 0.36 mmol). The reaction was stirred for 1 hr and then ethyl chloroformate (0.060 mL, 60 mmol) was added via syringe. The reaction was allowed to warm to rt for 1 hr and was then quenched with aq. sodium bicarbonate and extracted twice with ethyl acetate. The organic layers were washed with brine, dried over sodium sulfate, and evaporated. The residue was purified by Prep TLC (2×1 mm, silica) (25% ethyl acetate in hexanes) to afford the title compound.

HPLC/MS: 409 (M+1), 411 (M+3); $R_t$=4.19 min.

Step E: N-(Piperidin-1-yl)-4-(4-chlorophenyl)-5-(2,4-dichlorophenyl)-1-methylimidazole-2-carboxamide A mixture of ethyl 4-(4-chlorophenyl)-5-(2,4-dichlorophenyl)-1-methylimidazole-2-carboxylate (50 mg, 0.125 mmol) from Step D in neat 1-aminopiperidine (1 mL) was heated at 90° C. for 72 hr. Most of the amine was evaporated under a stream of nitrogen and the residue was purified by Prep TLC (2×1 mm, silica) (40% ethyl acetate in hexanes to afford the title compound.

HPLC/MS: 463 (M+1), 465 (M+3); $R_t$=3.81 min.

EXAMPLE 33

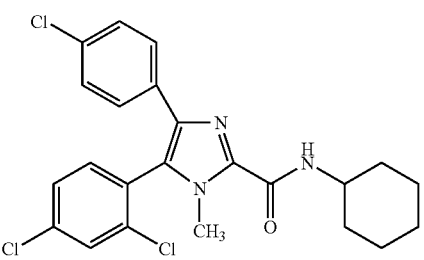

N-(Cyclohexyl)-4-(4-chlorophenyl)-5-(2,4-dichlorophenyl)-1-methylimidazole-2-carboxamide To a solution of 4-(4-chlorophenyl)-5-(2,4-dichlorophenyl)-1-methylimidazole (50 mg, 0.15 mmol) from Example 32, Step C in THF (3 mL) cooled to −70° C. in a dry ice/acetone bath was added 1.6N n-butyl lithium in hexanes (0.11 mL, 0.18 mmol). The reaction was stirred for 1 hr and then cyclohexyl isocyanate (0.040 mL, 30 mmol) was added via syringe. The reaction was allowed to warm to rt for 1 hr and was then quenched with aq. sodium bicarbonate and extracted twice with ethyl acetate. The organic layers were washed with brine, dried over sodium sulfate, and evaporated. The residue was purified by Prep TLC (1 mm, silica) (100% methylene chloride) to afford the title compound.

HPLC/MS: 462 (M+1), 464 (M+3); $R_t$=5.17 min.; $^1$HNMR (CDCl$_3$): 1.2-1.8 (4m, 6H), 1.85 (dt, 2H), 2.05 (m, 2H), 3.92 (s, 3H), 3.96 (m, 1H), 7.24 (d, J=8.2 Hz, 1H), 7.31 (br d, J=8.2 Hz, 2H), 7.44 (dd, J=2.0 and 8.2 Hz, 1H), 7.47 (br d, J=8.2 Hz, 2H), 7.68 (d, J=2.0 Hz, 1H), 7.88 and 8.33 (2 d, J=8.8 Hz, 1H). The isomeric assignment was confirmed by an NOe between the N-Me and 6-H of the 5-(2,4-dichlorophenyl) at δ=7.24.

EXAMPLE 34

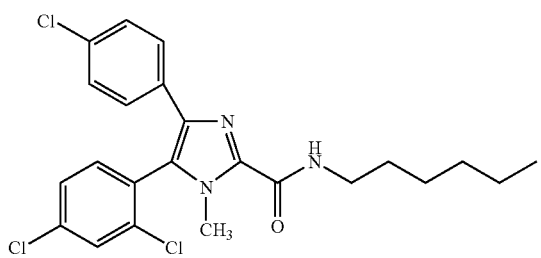

N-(Hexyl)-4-(4-chlorophenyl)-5-(2,4-dichlorophenyl)-1-methylimidazole-2-carboxamide Using essentially the same procedure as Example 33, but using n-hexyl isocyanate (0.040 mL, 0.30 mmol), 4-(4-chlorophenyl)-5-(2,4-dichlorophenyl)-1-methylimidazole (50 mg, 0.15 mmol) from Example 32, Step C was converted to the title compound after purification twice by Prep TLC (25% ethyl acetate in hexanes).

HPLC/MS: 464 (M+1), 466 (M+3); $R_t$=5.01 min.

EXAMPLE 35

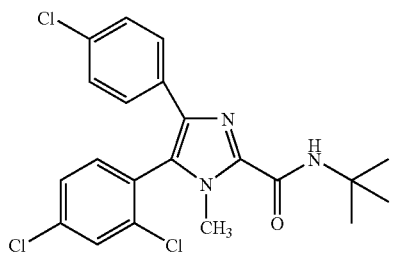

N-(t-Butyl)-4-(4-chlorophenyl)-5-(2,4-dichlorophenyl)-1-methylimidazole-2-carboxamide Using essentially the same procedure as Example 33, but using t-butyl isocyanate (0.040 mL, 0.30 mmol), 4-(4-chlorophenyl)-5-(2,4-dichlorophenyl)-1-methylimidazole (50 mg, 0.15 mmol) from Example 32, Step C was converted to the title compound after purification by Prep TLC (25% ethyl acetate in hexanes).

HPLC/MS: 436 (M+1), 438 (M+3); $R_t$=4.83 min.

EXAMPLE 36

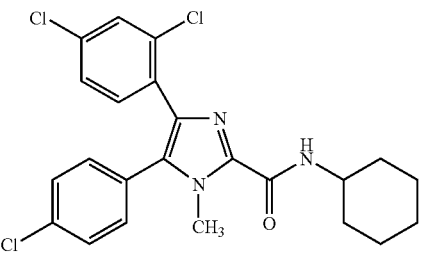

N-(Cyclohexyl)-4-(2,4-dichlorophenyl)-5-(4-chlorophenyl)-1-methylimidazole-2-carboxamide Method A To a solution of 4-(2,4-dichlorophenyl)-5-(4-chlorophenyl)-1-methylimidazole (50 mg, 0.15 mmol) from Example 32, Step C (lower Rf isomer) in THF (2.5 mL) cooled to −70° C. in a dry ice/acetone bath was added 1.6N n-butyl lithium in hexanes (0.120 mL, 0.18 mmol). The reaction was stirred for 1 hr and then cyclohexyl isocyanate (0.040 mL, 0.30 mmol) was added via syringe. The reaction was allowed to warm to rt for 1 hr and was then quenched with aq. sodium bicarbonate and extracted twice with ethyl acetate. The organic layers were washed with brine, dried over sodium sulfate, and evaporated. The residue was purified by Prep TLC (2×1 mm, silica) (25% ethyl acetate in hexanes) to afford the title compound.

HPLC/MS: 462 (M+1), 464 (M+3); $R_t$=4.80 min.; $^1$HNMR (CDCl$_3$): 1.2-1.7 (4m, 6H), 1.80 (m, 2H), 2.02 (m, 2H), 3.93 (m, 1H), 4.03 (s, 3H), 7.13 (dt, J=2.0 and 8.4 Hz, 2H), 7.265 (dd, J=2.1 and 8.4 Hz, 1H), 7.35 (d, J=8.4 Hz, 1H), 7.37 (m, 1H), 7.39 (dt, J=2.0 and 8.4 Hz, 2H), 7.9 (v br s, 1H). The isomeric assignment was confirmed by an NOe between the N-Me and the 2- and 6-H of the 5-(4-chlorophenyl) at δ=7.13.

Method B

Step A: Ethyl 4-(2,4-dichlorophenyl)-5-(4-chlorophenyl)-1-methylimidazole-2-carboxylate To a solution of 4-(2,4-dichlorophenyl)-5-(4-chlorophenyl)-1-methylimidazole (72 mg, 0.21 mmol) from Example 32, Step C (lower Rf isomer) in THF (3 mL) cooled to −70° C. in a dry ice/acetone bath was added 1.6N n-butyl lithium in hexanes (0.160 mL, 0.26 mmol). The reaction was stirred for 1 hr and then ethyl chloroformate (0.045 mL, 42 mmol) was added via syringe. The reaction was allowed to warm to rt for 1 hr and was then quenched with aq. sodium bicarbonate and extracted twice with ethyl acetate. The organic layers were washed with brine, dried over sodium sulfate, and evaporated. The residue was purified by Prep TLC (2×1 mm, silica) (25% ethyl acetate in hexanes) to afford the title compound.

HPLC/MS: 409 (M+1), 411 (M+3); $R_t$=3.92 min.

Step B: N-(Cyclohexyl)-4-(2,4-dichlorophenyl)-5-(4-chlorophenyl)-1-methylimidazole-2-carboxamide A mixture of ethyl 4-(2,4-dichlorophenyl)-5-(4-chlorophenyl)-1-methylimidazole-2-carboxylate (20 mg, 0.05 mmol) from Step A in neat cyclohexylamine (2 mL) was heated at 90° C. for 72 hr. Most of the amine was evaporated under a stream of nitrogen and the residue was purified by Prep TLC (1 mm, silica) (25% ethyl acetate in hexanes to afford the title compound.

HPLC/MS: 462 (M+1), 464 (M+3); $R_t$=4.80 min.

EXAMPLE 37

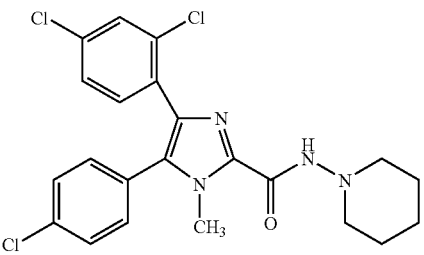

N-(Piperidin-1-yl)-4-(2,4-dichlorophenyl)-5-(4-chlorophenyl)-1-methylimidazole-2-carboxamide Using essentially the same procedure as Example 36, Step B (Method B), but using neat 1-aminopiperidine (3 mL), ethyl 4-(2,4-dichlorophenyl)-5-(4-chlorophenyl)-1-methylimidazole-2-carboxylate (30 mg, 0.073 mmol) was converted to the title compound after purification by Prep TLC (40% ethyl acetate in hexanes).

HPLC/MS: 463 (M+1), 465 (M+3); $R_t$=3.63 min.

EXAMPLE 38

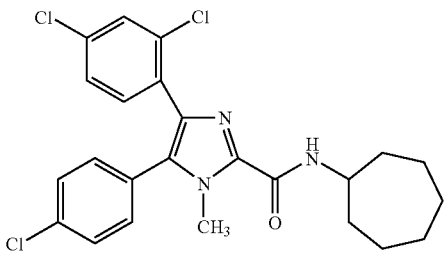

N-(Cycloheptyl)-4-(2,4-dichlorophenyl)-5-(4-chlorophenyl)-1-methylimidazole-2-carboxamide Using essentially the same procedure as Example 36, Step B (Method B), but using neat cycloheptylamine (1.5 mL), ethyl 4-(2,4-dichlorophenyl)-5-(4-chlorophenyl)-1-methylimidazole-2-carboxylate (30 mg, 0.073 mmol) was converted to the title compound after purification by Prep TLC (25% ethyl acetate in hexanes).

HPLC/MS: 476 (M+1), 478 (M+3); $R_t$=4.96 min.

EXAMPLE 39

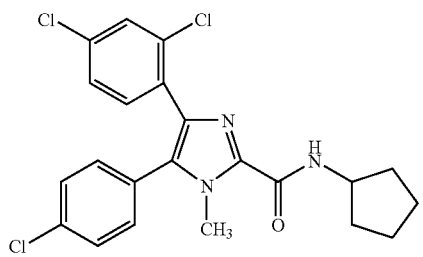

N-(Cyclopentyl)-4-(2,4-dichlorophenyl)-5-(4-chlorophenyl)-1-methylimidazole-2-carboxamide Using essentially the same procedure as Example 36, Step B (Method B), but using neat cyclopentylamine (1.5 mL), ethyl 4-(2,4-dichlorophenyl)-5-(4-chlorophenyl)-1-methylimidazole-2-carboxylate (30 mg, 0.073 mmol) was converted to the title compound after purification by Prep TLC (25% ethyl acetate in hexanes).

HPLC/MS: 448 (M+1), 450 (M+3); $R_t$=4.61 min.

EXAMPLE 40

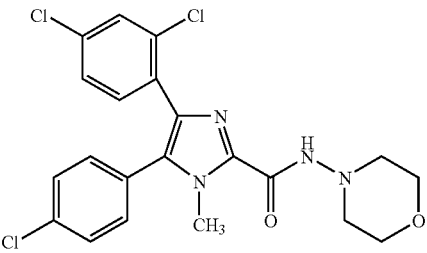

N-(Morpholin-4-yl)-4-(2,4-dichlorophenyl)-5-(4-chlorophenyl)-1-methylimidazole-2-carboxamide Using essentially the same procedure as Example 36, Step B (Method B), but using neat morpholine (1.5 mL), ethyl 4-(2,4-dichlorophenyl)-5-(4-chlorophenyl)-1-methylimidazole-2-carboxylate (30 mg, 0.073 mmol) was converted to the title compound after purification by Prep TLC (60% ethyl acetate in hexanes).

HPLC/MS: 465 (M+1), 467 (M+3); $R_t$=3.44 min.

EXAMPLE 41

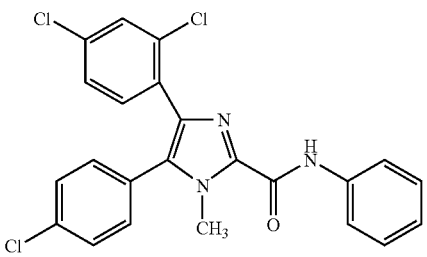

N-(Phenyl)-4-(2,4-dichlorophenyl)-5-(4-chlorophenyl)-1-methylimidazole-2-carboxamide Using essentially the same procedure as Example 36, Method A, but using phenyl isocyanate (0.023 mL, 0.21 mmol), 4-(2,4-dichlorophenyl)-5-(4-chlorophenyl)-1-methylimidazole (35 mg, 0.10 mmol) was converted to the title compound after purification by Prep TLC (25% ethyl acetate in hexanes).

HPLC/MS: 456 (M+1), 458 (M+3); $R_t$=4.75 min.

EXAMPLE 42

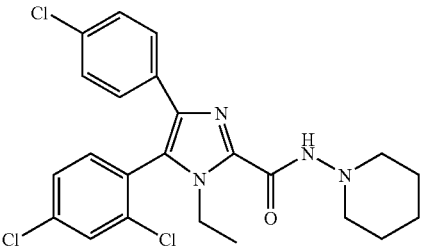

N-(Piperidin-1-yl)-4-(4-chlorophenyl)-5-(2,4-dichlorophenyl)-1-ethylimidazole-2-carboxamide Step A: 4-(4-Chlorophenyl)-5-(2,4-dichlorophenyl)-1-ethylimidazole (Higher Rf Isomer) and 4-(2,4-dichlorophenyl)-5-(4-chlorophenyl)-1-ethylimidazole (Lower Rf Isomer)

To a solution of 4-(4-chlorophenyl)-5-(2,4-dichlorophenyl)imidazole (400 mg, 1.24 mmol) from Example 32, Step B and ethyl iodide (0.200 mL, 2.5 mmol) in DMF (6 mL) was added sodium hydride (60% in mineral oil, 124 mg, 3.1 mmol). The reaction was stirred at rt for 1 hr and was then quenched with aq. sodium bicarbonate and extracted twice with ethyl acetate. The organic layers were washed with brine, dried over sodium sulfate, and evaporated. The residue was purified by flash chromatography (50-75% ethyl acetate in hexanes) to afford the title higher Rf compound.

HPLC/MS: 351 (M+1), 353 (M+3); $R_t$=2.9 min

Further elution with 100% ethyl acetate afforded a mixture of isomers which were further separated by Prep TLC (3×1 mm, silica) (100% ethyl acetate) to give additional higher Rf isomer (85 mg, 18%) and pure lower Rf isomer.

HPLC/MS: 351 (M+1), 353 (M+3); $R_t$=2.9 min.

Step B: Ethyl 4-(4-chlorophenyl)-5-(2,4-dichlorophenyl)-1-ethylimidazole-2-carboxylate To a solution of 4-(4-chlorophenyl)-5-(2,4-dichlorophenyl)-1-ethylimidazole (230 mg, 0.66 mmol) from Step A (higher Rf isomer) in THF (4 mL) cooled to −70° C. in a dry ice/acetone bath was added 1.6N n-butyl lithium in hexanes (0.500 mL, 0.80 mmol). The reaction was stirred for 1 hr and then ethyl chloroformate (0.130 mL, 1.3 mmol) was added via syringe. The reaction was allowed to warm to rt for 1 hr and was then quenched with aq. sodium bicarbonate and extracted twice with ethyl acetate. The organic layers were washed with brine, dried over sodium sulfate, and evaporated. The residue was purified by Prep TLC (3×1 mm, silica) (25% ethyl acetate in hexanes) to afford the title compound.

HPLC/MS: 423 (M+1), 425 (M+3); $R_t$=4.37 min.

Step C: N-(Piperidin-1-yl)-4-(4-chlorophenyl)-5-(2,4-dichlorophenyl)-1-ethylimidazole-2-carboxamide A mixture of ethyl 4-(4-chlorophenyl)-5-(2,4-dichlorophenyl)-1-ethylimidazole-2-carboxylate (25 mg, 0.06 mmol) from Step B in neat 1-aminopiperidine (2 mL) was heated at 90° C. for 72 hr. Most of the amine was evaporated under a stream of nitrogen and the residue was purified by Prep TLC (1 mm, silica) (25% ethyl acetate in hexanes) to afford the title compound.

HPLC/MS: 477 (M+1), 479 (M+3); $R_t$=4.03 min.

EXAMPLE 43

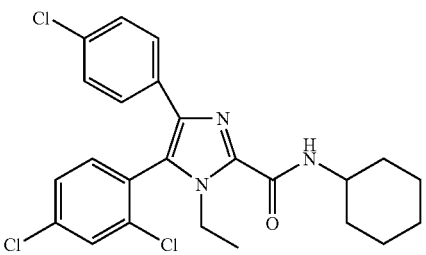

N-(Cyclohexyl)-4-(4-chlorophenyl)-5-(2,4-dichlorophenyl)-1-ethylimidazole-2-carboxamide Using essentially the same procedure as Example 42, Step C, but using neat cyclohexylamine (2 mL), ethyl 4-(4-chlorophenyl)-5-(2,4-dichlorophenyl)-1-ethylimidazole-2-carboxylate (30 mg, 0.073 mmol) from Example 42, Step B was converted to the title compound after purification by Prep TLC (25% ethyl acetate in hexanes).

HPLC/MS: 476 (M+1), 478 (M+3); $R_t$=5.04 min.

EXAMPLE 44

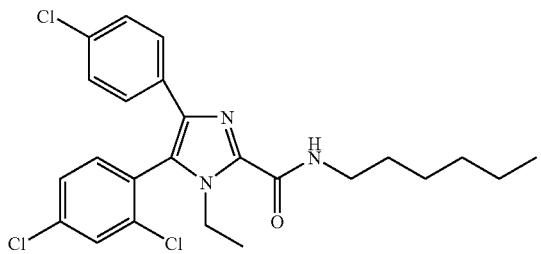

N-(Hexyl)-4-(4-chlorophenyl)-5-(2,4-dichlorophenyl)-1-ethylimidazole-2-carboxamide Using essentially the same procedure as Example 42, Step C, but using neat hexylamine (2 mL), ethyl 4-(4-chlorophenyl)-5-(2,4-dichlorophenyl)-1-ethylimidazole-2-carboxylate (25 mg, 0.060 mmol) from Example 42, Step B was converted to the title compound after purification by Prep TLC (25% ethyl acetate in hexanes).

HPLC/MS: 478 (M+1), 480 (M+3); $R_t$=5.23 min.

EXAMPLE 45

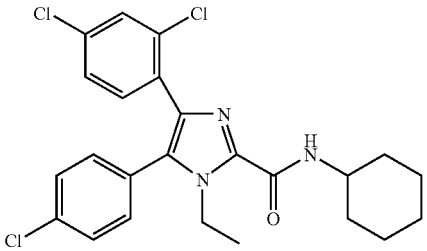

N-(Cyclohexyl)-4-(2,4-dichlorophenyl)-5-(4-chlorophenyl)-1-ethylimidazole-2-carboxamide A solution of 4-(2,4-dichlorophenyl)-5-(4-chlorophenyl)-1-ethylimidazole (43 mg, 0.12 mmol) from Example 41, Step A (lower Rf isomer) in THF (2 mL) cooled to −70° C. in a dry ice/acetone bath was added 1.6N n-butyl lithium in hexanes (0.092 mL, 0.15 mmol). The reaction was stirred for 1 hr and then cyclohexyl isocyanate (0.032 mL, 0.25 mmol) was added via syringe. The reaction was allowed to warm to rt for 1 hr and was then quenched with aq. sodium bicarbonate and extracted twice with ethyl acetate. The organic layers were washed with brine, dried over sodium sulfate, and evaporated. The residue was purified by Prep TLC (3×1 mm, silica) (25% ethyl acetate in hexanes) to afford the title compound.

HPLC/MS: 476 (M+1), 478 (M+3); $R_t$=4.99 min.

EXAMPLE 46

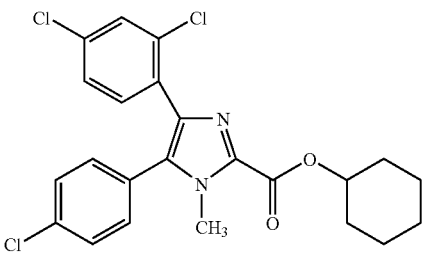

Cyclohexyl 4-(2,4-dichlorophenyl)-5-(4-chlorophenyl)-1-methylimidazole-2-carboxylate To a solution of ethyl 4-(2,4-dichlorophenyl)-5-(4-chlorophenyl)-1-methylimidazole-2-carboxylate (28 mg, 0.07 mmol) from Example 36, Step A (Method B) in cyclohexanol (2 mL) and methylene chloride (1 mL) was added a catalytic amount of sodium hydride (60% in mineral oil, <5 mg). The mixture was stirred at rt for 2 hr and then poured into aq. sodium bicarbonate and extracted twice with ethyl acetate. The organic layers were washed with brine, dried over sodium sulfate, and evaporated. The residue was purified by Prep TLC (3×1 mm, silica) (25% ethyl acetate in hexanes) to afford the title compound.

HPLC/MS: 463 (M+1), 465 (M+3); $R_t$=4.50 min.

EXAMPLE 47

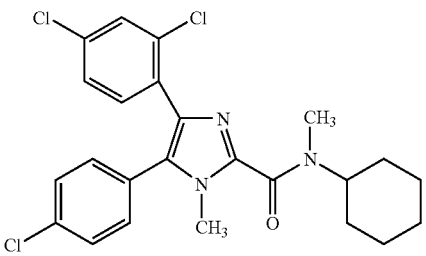

N-Methyl-N-cyclohexyl-4-(2,4-dichlorophenyl)-5-(4-chlorophenyl)-1-methylimidazole-2-carboxamide To a solution of N-cyclohexyl-4-(2,4-dichlorophenyl)-5-(4-chlorophenyl)-1-methylimidazole-2-carboxamide (15 mg, 0.033 mmol) from Example 36, (Method A) and methyl iodide (0.003 mL, 0.049 mmol) in DMF (2 mL) was added sodium hydride (60% in mineral oil, 2 mg, 0.049 mmol). The mixture was stirred at rt for 2 hr and then poured into aq. sodium bicarbonate and extracted twice with ethyl acetate. The organic layers were washed with brine, dried over sodium sulfate, and evaporated. The residue was purified by Prep TLC (0.5 mm, silica) (25% ethyl acetate in hexanes) to afford the title compound.

HPLC/MS: 476 (M+1), 478 (M+3); $R_t$=4.40 min.

EXAMPLE 48

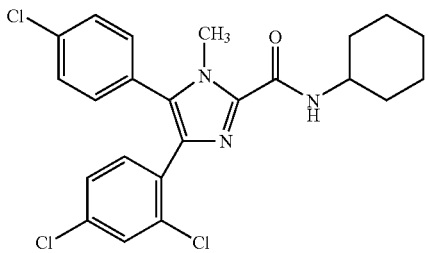

N-(Cyclohexyl)-4-(2,4-dichlorophenyl)-5-(4-chlorophenyl)-1-methylimidazole-2-carboxamide Step A: 2-(4-Chlorophenyl)-1-(2,4-dichlorophenyl)ethanone A 5 L round bottom flask equipped with an addition funnel, $N_2$ inlet, thermometer and a mechanical stirrer was charged with 387 mL of 1M sodium bis-trimethylsilylamide in TBF and cooled to −60° C. A solution of 230 g (1.35 mol) of 4-chlorophenylacetic acid in 300 mL of THF was added keeping the temperature below −40° C. After stirring the mixture for 90 min at −70° C., 264 g (1.29 mol) of methyl 2,4-dichlorobenzoate was added over 20 min. The solution was stirred for 40 min at −70° C., the cooling bath was removed and the mixture was allowed to warm to 0° C. Reaction was quenched by pouring into 4 L of 2N HCl and ice and extracted with ether. Each ether layer was washed with saturated $NaHCO_3$, brine, dried with $MgSO_4$ and filtered through a 2" plug of silica gel. The filtrate was concentrated to ca. 1 lit of a slushy liquid which was diluted with 1 L of hexane and cooled in a refrigerator. The solid formed was filtered, washed with hexane and dried. A second crop was isolated by concentrating the mother liquors. The two crops of crystals were combined.

$^1$H NMR: (500 MHz, $CDCl_3$): δ 4.21 (s, 2H), 7.2-7.5 (m, 7H).

Step B: 1-(4-Chlorophenyl)-2-(2,4-dichlorophenyl)ethane-1,2-dione

To a solution of 100 g (0.33 mol) of 2-(4-chlorophenyl)-1-(2,4-dichlorophenyl)ethanone in 1 L of DMSO, 75 g (0.42 mol) of NBS was added and the mixture was stirred over a weekend. The reaction was poured into 8 L of water and stirred for 30 min. The yellow solid formed was filtered and dried. This solid was purified by passing through a plug of 1 Kg of silica gel using hexane and 5% EtOAc-hexane to isolate the title compound.

$^1$H NMR: (500 MHz, $CDCl_3$): δ 7.4-8.0 (m, 7H).

Step C: 5-(4-Chlorophenyl)-4-(2,4-dichlorophenyl)-1-methyl-imidazole

A solution of 10 g (31.8 mmol) of 1-(4-chlorophenyl)-2-(2,4-dichlorophenyl)ethane-1,2-dione in 30 mL of acetic acid was treated with 15 g (223 mmol) of methylamine hydrochloride, 5 g (63.7 mmol) of $NH_4OAc$ and 7.8 mL (93.6 mmol) of aqueous formaldehyde (37%). The mixture was refluxed over night, cooled and quenched by adding aq. NaOH (final pH 8). The solution was extracted with EtOAc and each EtOAc layer was washed with brine, dried and concentrated. The residue was purified on a flash column with a gradient of 50-100% EtOAc-hexane followed by 5% MeOH-EtOAc to yield 4-(4-chlorophenyl)-5-(2,4-dichlorophenyl)-1-methyl-imidazole (higher Rf, $^1$H NMR (500 MHz, $CDCl_3$) δ 3.47 (s, 3H), 7.22-7.24 (m, 2H), 7.26-7.28 (m, 1H), 7.36-7.39 (m, 3H), 7.64-7.65 (m, 2H)) and 3.5 g of 5-(4-chlorophenyl)-4-(2,4-dichlorophenyl)-1-methyl-imidazole (lower Rf, $^1$H NMR (500 MHz, $CDCl_3$) for lower Rf: δ 3.66 (s, 3H), 7.12-7.14 (m, 2H), 7.19-7.23 (m, 1H), 7.26-7.29 (m, 1H), 7.35-7.38 (m, 3H), 7.64 (s, 1H).

Step D: N-(Cyclohexyl)-4-(2,4-dichlorophenyl)-5-(4-chlorophenyl)-1-methylimidazole-2-carboxamide A solution of 5.5 g (16.2 mmol) of 5-(4-chlorophenyl)-4-(2,4-dichlorophenyl)-1-methyl-imidazole in 70 mL of THF was cooled in a −78° C. bath and 15 mL of 1.6 M n-BuLi was slowly added. After stirring for 1 h, 5.2 mL (40.7 mmol) of cyclohexylisocyanate was added. The cooling bath was removed and the solution was stirred for 3 h. The reaction mixture was poured into a mixture of water/EtOAc. The layers were separated and the aqueous layer was extracted with EtOAc. The combined organic layer was washed with brine, dried and concentrated. The residue was purified on a flash column using a gradient of 2-10% EtOAc-hexane. The isolated product was crystallized from EtOAc-hexane (~1:10) to obtain the title compound as a white solid with a melting point of 165° C.

$^1$H NMR (500 MHz, $CDCl_3$): δ 1.20-1.37 (m, 3H), 1.40-1.49 (m, 2H), 1.67-1.71 (m, 1H), 1.80-1.84 (m, 2H), 2.03-2.06 (m, 2H), 4.02 (s, 3H), 7.13-7.15 (m, 2H), 7.25-7.27 (m, 1H), 7.31-7.33 (m, 1H), 7.37-7.40 (m, 4H). LC-MS: $R_t$=4.7 min. m/e=464.1 (M+1). Further elution allowed recovery of starting material.

The following compounds were synthesized by the procedure of example 48 by substituting an appropriate amine or amine hydrochloride for methylamine in step C.

| Ex. No. | Name | Structure | retention time (min) | HPLC-mass spectrum m/e |
|---|---|---|---|---|
| 49 | N-(Cyclohexyl)-4-(2,4-dichlorophenyl)-5-(4-chlorophenyl)-1-ethylimidazole-2-carboxamide | 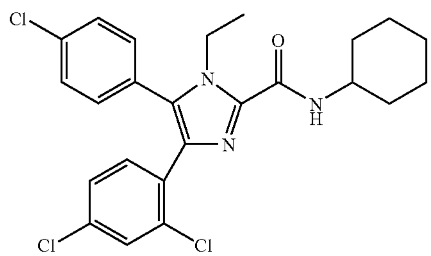 | 4.9 | 476.1 |
| 50 | N-(Cyclohexyl)-4-(2,4-dichlorophenyl)-5-(4-chlorophenyl)-1-(1-methyl)ethyl-imidazole-2-carboxamide | 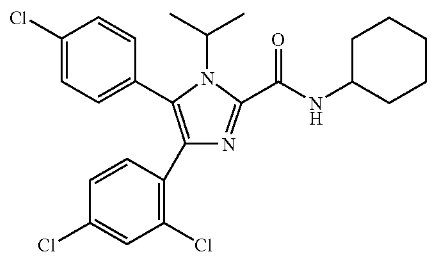 | 4.9 | 492.1 |
| 51 | N-(Cyclohexyl)-4-(2,4-dichlorophenyl)-5-(4-chlorophenyl)-1-(1,1-dimethyl)ethyl-imidazole-2-carboxamide | 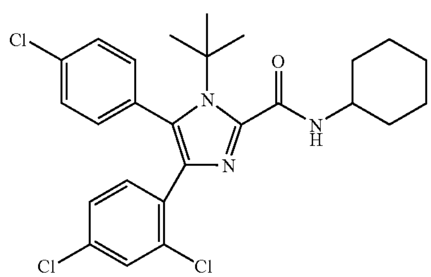 | 4.1 | 504.0 |
| 52 | N-(Cyclohexyl)-4-(2,4-dichlorophenyl)-5-(4-chlorophenyl)-1-(2-dimethylamino)ethyl-imidazole-2-carboxamide | 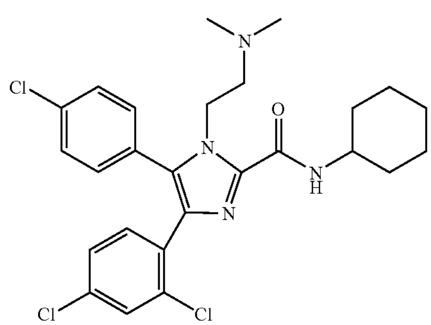 | 3.4 | 521.0 |
| 53 | N-(Cyclohexyl)-4-(2,4-dichlorophenyl)-5-(4-chlorophenyl)-1-propylimidazole-2-carboximide | 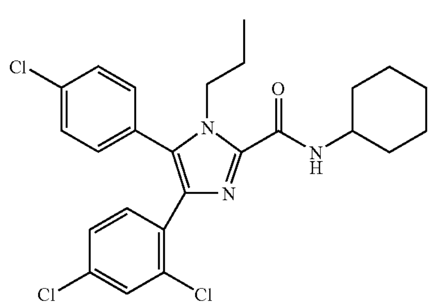 | 5.0 | 490.1 |

-continued

| Ex. No. | Name | Structure | retention time (min) | HPLC-mass spectrum m/e |
|---|---|---|---|---|
| 54 | N-(Cyclohexyl)-4-(2,4-dichlorophenyl)-5-(4-chlorophenyl)-1-butylimidazole-2-carboxamide | 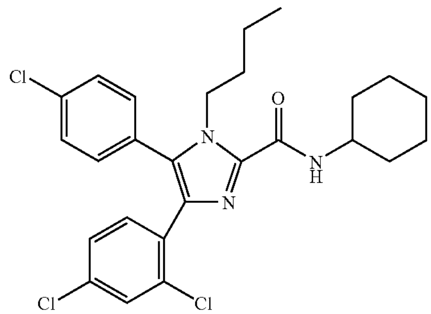 | 5.2 | 503.9 |
| 55 | N-(Cyclohexyl)-4-(2,4-dichlorophenyl)-5-(4-chlorophenyl)-1-(2-methoxy)ethylimidazole-2-carboxamide | 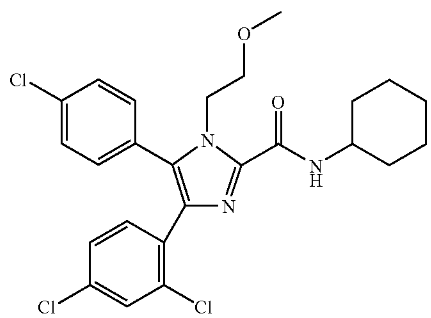 | 4.7 | 505.9 |

EXAMPLE 56

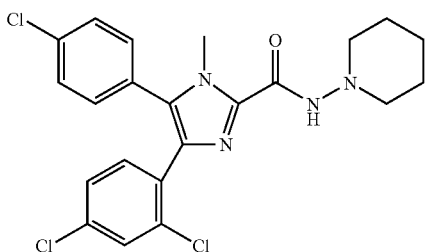

N-(Piperidin-1-yl)-5-(4-chlorophenyl)-4-(2,4-dichlorophenyl)-1-methyl-imidazole-2carboxamide Step A: Ethyl 4-(2,4-dichlorophenyl)-5-(4-chlorophenyl)-1-methylimidazole-2-carboxylate A solution of 1.1 g (3.25 mmol) of 5-(4-chlorophenyl)-4-(2,4-dichlorophenyl)-1-methyl-imidazole in 30 mL of dry THF was cooled in a −78° C. bath and 1.7 mL of 2.5 M n-BuLi in hexane was dropwise added. After stirring the solution for 1 h it was added with a canula to 0.623 mL of ethyl chloroformate in THF cooled in a −78° C. bath. The cold bath was removed and the reaction was stirred for 1 h then quenched with water. The mixture was extracted with EtOAc. The EtOAc layer was washed with brine, dried and concentrated. The residue was chromatographed using a gradient of 10-20% EtOAc-hexane to isolate the desired product.

$^1$H NMR (500 MHz, CDCl$_3$): δ 1.49 (t, 3H), 3.98 (s, 3H), 4.50 (q, 2H), 7.15-7.17 (m, 2H), 7.24-7.26 (m, 1H), 7.35-7.41 (m, 4H).

Step B: N-(Piperidin-1-yl)-5-(4-chlorophenyl)-4-(2,4-dichlorophenyl)-1-methyl-imidazole-2-carboxamide To a solution of 0.33 mL (3.05 mmol) of 1-aminopiperidine in 2 mL of dry toluene under N$_2$, 1.5 mL (3.05 mmol) of 2M trimethylaluminum in hexane was added with cooling in ice bath. The cold bath was removed, reaction was stirred for 1 h and 0.5 g (1.22 mmol) of ethyl 4-(2,4-dichlorophenyl)-5-(4-chlorophenyl)-1-methylimidazole-2-carboxylate in 3 mL of toluene, and 1.5 mL of CH$_2$Cl$_2$ was added. The mixture was heated in a 60° C. bath for 2 h, cooled, quenched with water and the pH was adjusted to 5 with 1.2 N HCl. The solution was extracted with EtOAc twice. The combined EtOAc layer was washed with brine, dried and concentrated. The residue was purified by flash chromatography using 30% EtOAc/hexane as an eluant to isolate the title compound.

$^1$H NMR (500 MHz, CDCl$_3$): δ 1.47 (m, 2H), 1.77-1.82 (m, 4H), 2.89 (s, 4H), 4.00 (s, 3H), 7.11-7.14 (m, 2H), 7.23-7.26 (m, 1H), 7.28-7.30 (m, 1H), 7.36-7.39 (m, 3H), 8.15 (s, 1H). LC-MS: R$_t$=3.6 min. m/e=465.1 (M+1).

The following compounds were prepared according to the procedure of example 56, by substituting an appropriate amine for 1-aminopiperidine in step B.

| Ex. No. | Name | Structure | retention time (min) | HPLC-mass spectrum m/e |
|---|---|---|---|---|
| 57 | N-(Pyrrolidin-1-yl)-5-(4-chlorophenyl)-4-(2,4-dichlorophenyl)-1-methyl-imidazole-2-carboxamide | 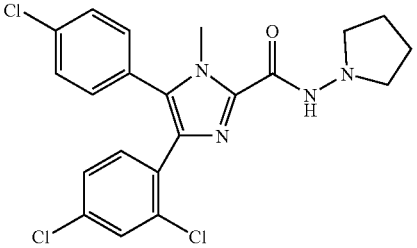 | 3.1 | 451.1 |
| 58 | N-(Azepin-1-yl)-5-(4-chlorophenyl)-4-(2,4-dichlorophenyl)-1-methyl-imidazole-2-carboxamide | 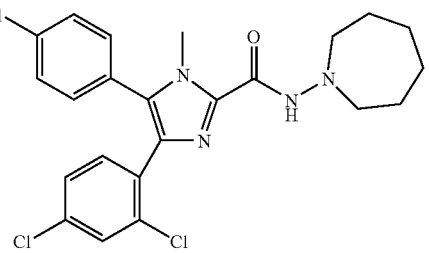 | 3.6 | 479.2 |
| 59 | N-(Pentyl)-4-(2,4-dichlorophenyl)-5-(4-chlorophenyl)-1-methylimidazole-2-carboximide | 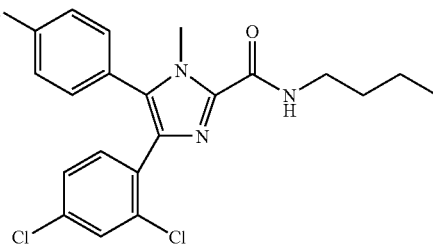 | 4.7 | 452.1 |
| 60 | N-(1-Ethylpropyl)-4-(2,4-dichlorophenyl)-5-(4-chlorophenyl)-1-methylimidazole-2-carboxamide | 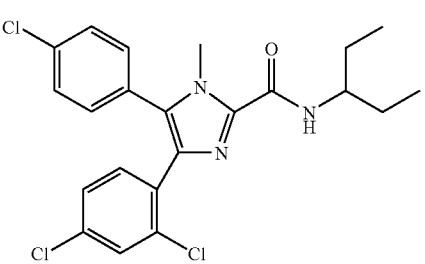 | 4.64 | 452.1 |
| 61 | N-(1-Methylethyl)-4-(2,4-dichlorophenyl)-5-(4-chlorophenyl)-1-methylimidazole-2-carboxamide | 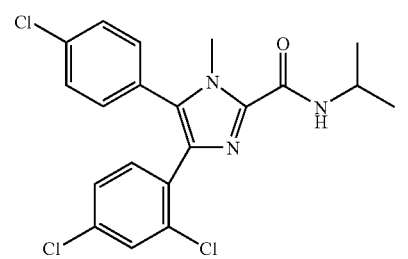 | 4.2 | 424.0 |
| 62 | N-(3-Cyclohexenyl)-4-(2,4-dichlorophenyl)-5-(4-chlorophenyl)-1-methylimidazole-2-carboxamide | 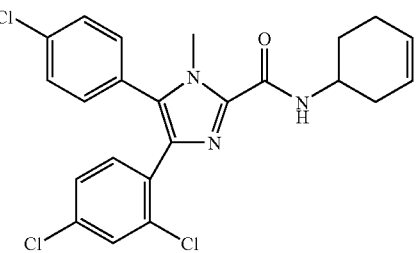 | 4.6 | 460.0 |

-continued

| Ex. No. | Name | Structure | retention time (min) | HPLC-mass spectrum m/e |
|---|---|---|---|---|
| 63 | N-(Tetrahydropyran-4-yl)-4-(2,4-dichlorophenyl)-5-(4-chlorophenyl)-1-methylimidazole-2-carboxamide | 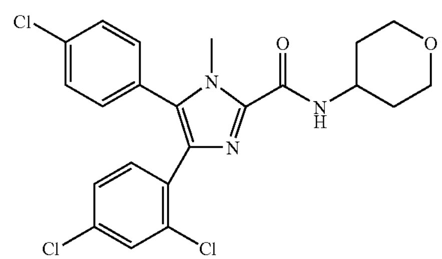 | 3.9 | 465.8 |
| 64 | N-(2,2-Dimethyl-tetrahydropyran-4-yl)-4-(2,4-dichlorophenyl)-5-(4-chlorophenyl)-1-methylimidazole-2-carboxamide | 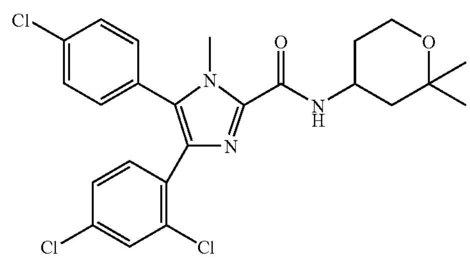 | 4.2 | 493.8 |
| 65 | N-((2-Trans-hydroxymethyl)cyclohexyl)-4-(2,4-dichlorophenyl)-5-(4-chlorophenyl)-1-methylimidazoile-2-carboxamide | 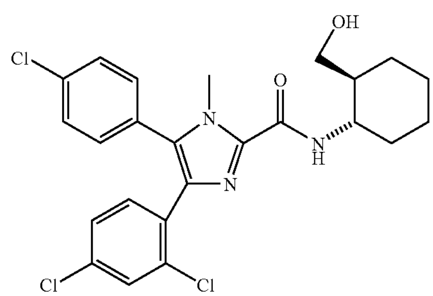 | 4.3 | 494.0 |
| 66 | N-((2-Cis-hydroxymethyl)cyclohexyl)-4-(2,4-dichlorophenyl)-5-(4-chlorophenyl)-1-methylimidazole-2-carboxamide | 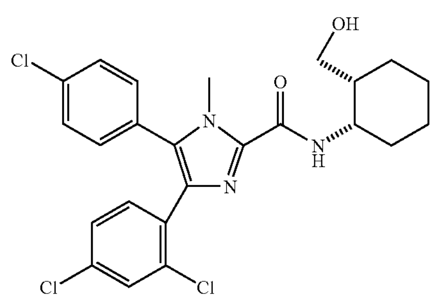 | 4.1 | 494.0 |
| 67 | N-((2-Trans-hydroxy)cyclohexyl)-4-(2,4-dichlorophenyl)-5-(4-chlorophenyl)-1-methylimidazole-2-carboxamide | 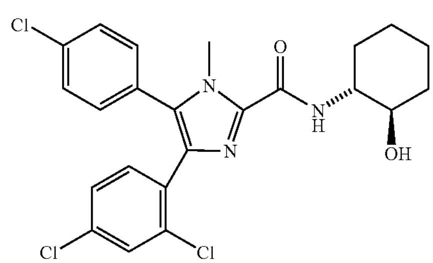 | 3.9 | 478.0 |

| Ex. No. | Name | Structure | retention time (min) | HPLC-mass spectrum m/e |
|---|---|---|---|---|
| 68 | N-((2-Cis-hydroxy)cyclohexyl)-4-(2,4-dichlorophenyl)-5-(4-chlorophenyl)-1-methylimidazole-2-carboxamide | 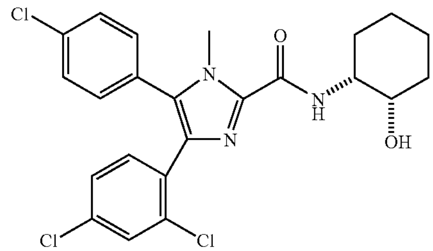 | 4.0 | 480.0 |
| 69 | N-((4-Trans-hydroxy)cyclohexyl)-4-(2,4-dichlorophenyl)-5-(4-chlorophenyl)-1-methylimidazole-2-carboxamide | 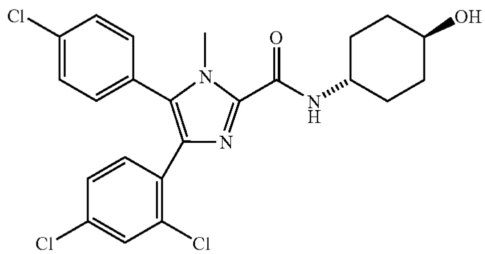 | 3.8 | 480.0 |
| 70 | N-(4-Methyl-cyclohexyl)-4-(2,4-dichlorophenyl)-5-(4-chlorophenyl)-1-methylimidazole-2-carboxamide (Isomer A) | 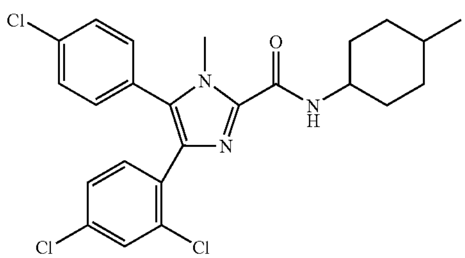 | 4.96 | 476.0 |
| 71 | N-(4-Methyl-cyclohexyl)-4-(2,4-dichlorophenyl)-5-(4-chlorophenyl)-1-methylimidazole-2-carboxamide (Isomer B) | 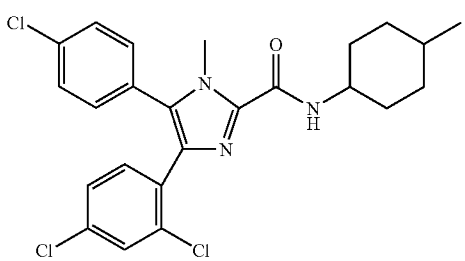 | 4.99 | 478.0 |
| 72 | N-(1-Fluoro-cyclohexen-4-yl)-4-(2,4-dichlorophenyl)-5-(4-chlorophenyl)-1-methylimidazole-2-carboxamide | 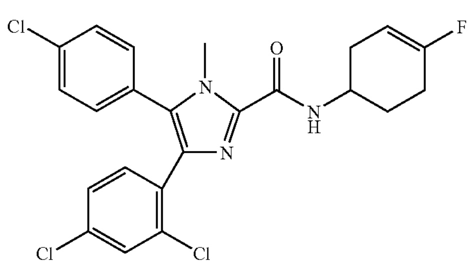 | 4.53 | 480.0 |

| Ex. No. | Name | Structure | retention time (min) | HPLC-mass spectrum m/e |
|---|---|---|---|---|
| 73 | N-(4,4-Difluoro-cyclohexyl)-4-(2,4-dichlorophenyl)-5-(4-chlorophenyl)-1-methylimidazole-2-carboxamide | 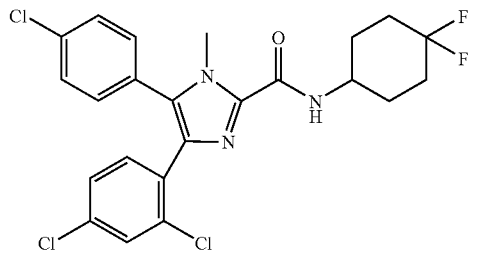 | 4.48 | 500.0 |

EXAMPLE 74

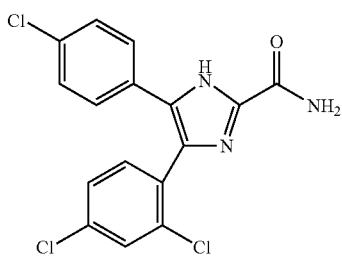

4-(2,4-Dichlorophenyl)-5-(4-chlorophenyl)-1-methylimidazole-2-carboxamide

The title compound was prepared from ethyl 4-(2,4-dichlorophenyl)-5-(4-chlorophenyl)-1-methylimidazole-2-carboxylate and 2 M $NH_3$ in MeOH following the method of example 36, step B (method B). LC-MS: $R_t$=3.6 min. m/e=379.9 (M+1).

EXAMPLE 75

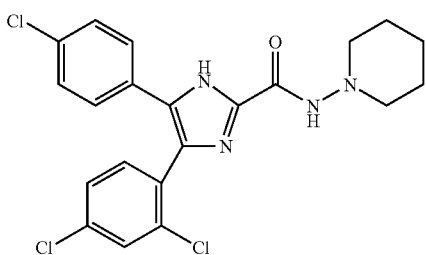

N-(Piperidin-1-yl)-5-(4-chlorophenyl)-4-(2,4-dichlorophenyl)-imidazole-2-carboxamide Step A 5-(4-chlorophenyl)-4-(2,4-dichlorophenyl)-1-{((2-trimethylsilyl)-ethoxy)methyl}-1H-imidazole To a solution of 5-(4-chlorophenyl)-4-(2,4-dichlorophenyl-1H-imidazole (500 mg, 1.54 mmol) in 3 mL of DMF sodium hydride (59 mg, 1.54 mmol) was added in portions over a period of 15 minutes. The mixture was allowed to stir until $H_2$ evolution ceased and it was clear. To this solution 2-(trimethylsilyl)ethoxy methyl chloride was added. After stirring overnight, the reaction was quenched with water and extracted with EtOAc. The organic layer was washed with water (3×20 mL), brine (1×30 mL), dried with $Na_2SO_4$, filtered, and concentrated to dryness. The residue was purified on a silica gel column eluting with hexane and 20% EtOAc/hexane to give the title compound.

$^1$H NMR (500 MHz, $CDCl_3$): δ 0.004 (s, 9H), 0.84-0.88 (m, 2H), 3.42 (t, 2H), 5.05 (d, 1H), 5.16 (d, 1H), 7.26 (d, 2H), 7.35 (d, 1H), 7.40-7.42 (m, 3H), 7.62 (d, 1H), 7.80 (s, 1H).

Step B N-Piperidin-1-yl-5-(4-chlorophenyl)-4-(2,4-dichlorophenyl)-1(((2-trimethylsilyl)ethoxy)methyl)-1H-imidazole-2-carboxamide The title compound was prepared from 5-(4-chlorophenyl)-4-(2,4-dichlorophenyl)-1-{((2-trimethylsilyl)ethoxy)methyl}-1H-imidazole as described in example 56, steps A and B.

$^1$H NMR (500 MHz, $CDCl_3$): δ −0.018 (s, 9H), 0.82-0.90 (m, 2H), 1.52 (m, 2H), 1.81-1.85 (m, 4H), 2.94 (s, 4H), 3.54-3.61 (m, 2H), 5.47 (d, 1H), 6.04 (d, 1H), 7.28 (d, 2H), 7.38-7.43 (m, 4H), 7.60 (d, 1H), 8.29 (s, 1H).

Step C N-(Piperidin-1-yl)-5-(4-chlorophenyl)-4-(2,4-dichlorophenyl)-imidazole-2-carboxamide To a solution of 5-(4-chlorophenyl)-4-(2,4-dichlorophenyl)-N-piperidin-1-yl-1-{((2-trimethylsilyl)ethoxy)methyl}-1H-imidazole-2-carboxamide (180 mg, 0.310 mmol) in 2 mL dichloromethane was added boron trifluoride diethyl etherate (393 μL, 3.10 mmol). After stirring overnight, the reaction was quenched with aqueous $K_2CO_3$. The aqueous layer was extracted with EtOAc (3×10 mL). The combined organic extract was washed with brine, dried over $Na_2SO_4$, filtered, and concentrated. The residue was purified by preparative HPLC to isolate the title compound.

$^1$H NMR (500 MHz, $CDCl_3$): δ 1.54 (m, 2H), 1.78-1.83 (m, 4H), 3.12-3.14 (m, 4H), 7.30 (m, 1H), 7.32-7.33 (m, 7H), 7.52 (d, 1H). LC-MS: $R_t$=3.4 min. m/e=450.9 (M+1).

The following analogs were prepared by the methods described in example 48 and/or example 56.

| Ex. No. | Name | Structure | retention time (min) | HPLC-mass spectrum m/e |
|---|---|---|---|---|
| 76 | N-(Piperidin-1-yl)-5-(4-chlorophenyl)-4-(2,4-dichlorophenyl)-1-ethyl-imidazole-2-carboxamide | 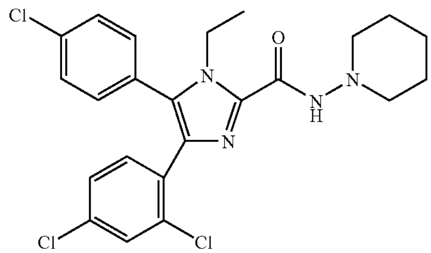 | 3.7 | 479.0 |
| 77 | N-(Piperidin-1-yl)-5-(4-chlorophenyl)-4-(2,4-dichlorophenyl)-1-(1-methyl)ethyl-imidazole-2-carboxamide | 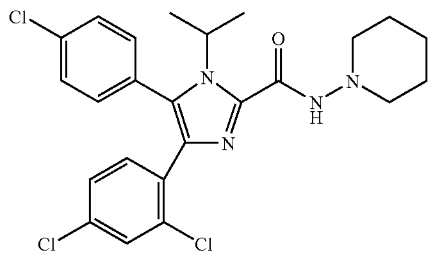 | 3.8 | 493.1 |
| 78 | N-(Piperidin-1-yl)-5-(4-chlorophenyl)-4-(2,4-dichlorophenyl)-1-(1,1-dimethyl)ethyl-imidazole-2-carboxamide | 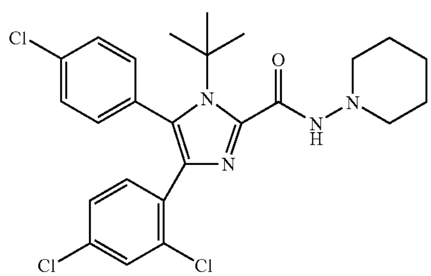 | 3.4 | 505.1 |
| 79 | N-(Piperidin-1-yl)-5-(4-chlorophenyl)-4-(2,4-dichlorophenyl)-1-(2-dimethylamino)ethyl-imidazole-2-carboxamide | 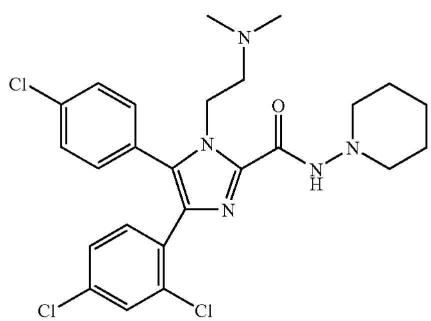 | 2.9 | 522.0 |
| 80 | N-(Piperidin-1-yl)-5-(4-chlorophenyl)-4-(2,4-dichlorophenyl)-1-propyl-imidazole-2-carboxamide | 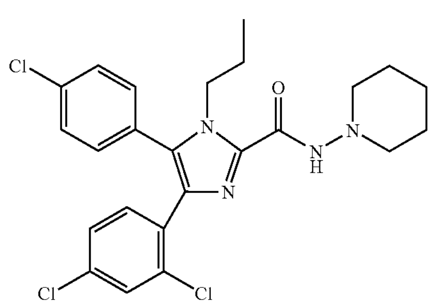 | 3.9 | 491.1 |

| Ex. No. | Name | Structure | retention time (min) | HPLC-mass spectrum m/e |
|---|---|---|---|---|
| 81 | N-(Piperidin-1-yl)-5-(4-chlorophenyl)-4-(2,4-dichlorophenyl)-1-butyl-imidazole-2-carboxamide | 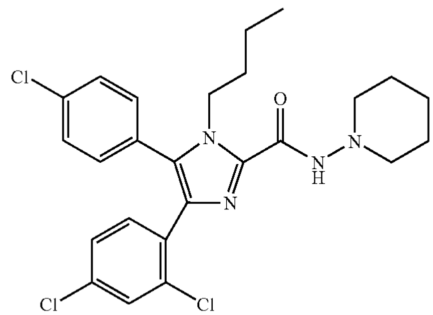 | 4.1 | 506.9 |
| 82 | N-(Piperidin-1-yl)-5-(4-chlorophenyl)-4-(2,4-dichlorophenyl)-1-(2-methoxy)ethyl-imidazole-2-carboxamide | 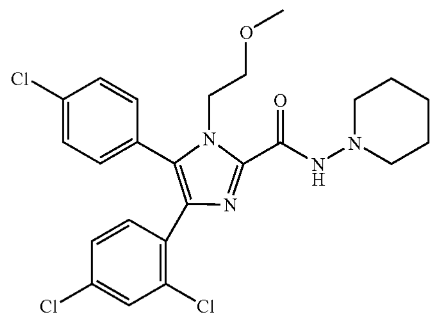 | 3.7 | 508.9 |
| 83 | N-(Cyclohexyl)-4-(2-chlorophenyl)-5-(4-chlorophenyl)-1-methylimidazole-2-carboxamide | 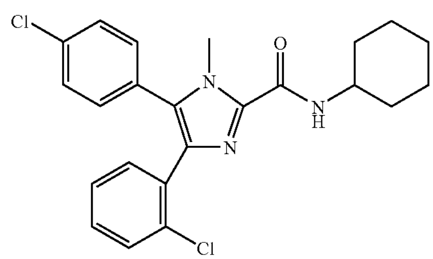 | 4.2 | 428.0 |
| 84 | N-(Piperidin-1-yl)-4-(2-chlorophenyl)-5-(4-chlorophenyl)-1-methyl-imidazole-2-carboxamide | 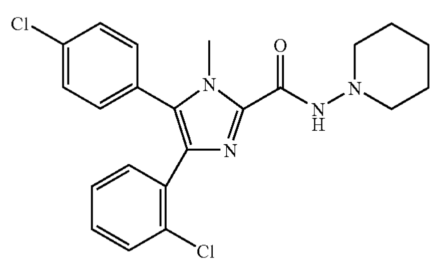 | 3.1 | 429.1 |

EXAMPLE 85

Cannabinoid Receptor-1 (CB1) Binding Assay

Binding affinity determination is based on recombinant human CB1 receptor expressed in Chinese Hamster Ovary (CHO) cells (Felder et al, Mol. Pharmacol. 48: 443450, 1995). Total assay volume is 250 μl (240 μl CB1 receptor membrane solution plus 5 μl test compound solution plus 5 μl [3H]CP-55940 solution). Final concentration of [3H]CP-55940 is 0.6 nM. Binding buffer contains 50 mM Tris-HCl, pH7.4, 2.5 mM EDTA, 5mM MgCl$_2$, 0.5 mg/ml fatty acid free bovine serum albumin and protease inhibitors (Cat#P8340, from Sigma). To initiate the binding reaction, 5 μl of radioligand solution is added, the mixture is incubated with gentle shaking on a shaker for 1.5 hours at 30° C. The binding is terminated by using 96-well harvester and filtering through GF/C filter presoaked in 0.05% polyethylenimine. The bound radiolabel is quantitated using scintillation counter. Apparent binding affinities for various compounds are calculated from IC50 values (DeBlasi et al., Trends Pharmacol Sci 10: 227-229, 1989).

The binding assay for CB2 receptor is done similarly with recombinant human CB2 receptor expressed in CHO cells.

EXAMPLE 86

Cannabinoid Receptor-1 (CB1) Functional Activity Assay

The functional activation of CB1 receptor is based on recombinant human CB1 receptor expressed in CHO cells (Felder et al, Mol. Pharmacol. 48: 443-450, 1995). To determine the agonist activity or inverse agonist activity of any test compound, 50 ul of CB1-CHO cell suspension are mixed with test compound and 70 ul assay buffer containing 0.34 mM 3-isobutyl-1-methylxanthine and 5.1 uM of forskolin in 96-well plates. The assay buffer is comprised of Earle's Balanced Salt Solution supplemented with 5 mM $MgCl_2$, 1 mM glutamine, 10 mM HEPES, and 1 mg/ml bovine serum albumin. The mixture is incubated at room temperature for 30 minutes, and terminated by adding 30 ul/well of 0.5M HCl. The total intracellular cAMP level is quantitated using the New England Nuclear Flashplate and cAMP radioimmunoassay kit.

To determine the antagonist activity of test compound, the reaction mixture also contains 0.5 nM of the agonist CP55940, and the reversal of the CP55940 effect is quantitated. Alternatively, a series of dose response curves for CP55940 is performed with increasing concentration of the test compound in each of the dose response curves.

The functional assay for the CB2 receptor is done similarly with recombinant human CB2 receptor expressed in CHO cells.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula (I):

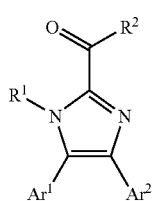

(I)

or a pharmaceutically acceptable salt thereof, wherein:
$R^1$ is selected from:
 (1) hydrogen
 (2) $C_{1-10}$alkyl,
 (3) $C_{2-10}$alkenyl,
 (4) $C_{2-10}$alkynyl,
 (5) cycloalkyl,
 (6) cycloalkyl-$C_{1-10}$alkyl,
wherein alkyl, alkenyl, alkynyl, and cycloalkyl, are optionally substituted with one to four substituents independently selected from $C_{1-4}$ alkoxy, amino, and $R^a$;
$R^2$ is selected from:
 (1) —$OR^d$, and
 (2) —$NR^dR^e$;
$Ar^1$ and $Ar^2$ are each independently selected from:
 (1) phenyl,
 (2) 4-chlorophenyl,
 (3) 4-methylphenyl, and
 (4) 2,4-dichlorophenyl;
each $R^a$ is independently selected from:
 (1) —$OR^d$,
 (2) —$NR^dS(O)_mR^e$,
 (3) —$S(O)_mR^d$,
 (4) —$SR^d$,
 (5) —$S(O)_mNR^dR^e$,
 (6) —$NR^dR^e$,
 (7) —$O(CR^fR^g)_nNR^dR^c$,
 (8) —$CO_2R^d$,
 (9) —$CO_2(CR^fR^g)_nCONR^dR^e$,
 (10) —$OC(O)R^d$,
 (11) —$C(O)NR^dR^e$,
 (12) —$NR^dC(O)R^e$,
 (13) —$OC(O)NR^dR^e$,
 (14) —$NR^dC(O)OR^e$,
 (15) —$NR^dC(O)NR^dR^e$, and
 (16) —$CR^d(N$—$OR^e)$;
wherein $R^d$ is selected from piperidinyl, morpholinyl, pyrrolidinyl, azepinyl, tetrahydropyranyl and 2,2-dimethyl tetrahydropyranyl; $R^e$ is selected from hydrogen and methyl; or $R^d$ and $R^e$ together with the nitrogen to which they are attached form a piperidinyl, pyrrolidinyl, or morpholinyl ring;
$R^f$ and $R^g$ are independently selected from hydrogen, $C_{1-10}$alkyl, cycloalkyl; and
cycloalkyl-$C_{1-10}$alkyl;
wherein cycloalkyl is selected from: cyclopropyl, cyclobutyl, cyclopentyl, cyclohexyl, and cycloheptyl;
m is selected from 1 and 2; and
n is selected from 1, 2, and 3.

2. The compound according to claim 1, wherein:
$R^1$ is $C_{1-10}$alkyl;
$R^2$ is as in claim 1;
$Ar^1$ is 4-chlorophenyl, and $Ar^2$ is 2,4-dichlorophenyl; and
$R^d$ is selected from piperidinyl, morpholinyl, and pyrrolidinyl; $R^e$ is selected from hydrogen and methyl; or $R^d$ and $R^e$ together with the nitrogen to which they are attached form a piperidinyl, pyrrolidinyl, or morpholinyl ring;
or a pharmaceutically acceptable salt thereof.

3. The compound according to claim 2, wherein:
$R^1$ is methyl;
$R^2$ is —$NR^dR^e$;
$Ar^1$ is 4-chlorophenyl, and $Ar^2$ is 2,4-dichlorophenyl;
$R^d$ is 1-piperidinyl;
or a pharmaceutically acceptable salt thereof.

4. A compound selected from:
 (1) N-(piperidin-1-yl)-4,5-diphenyl-1-methylimidazole-2-carboxamide,
 (2) 2-(piperidin-1-ylcarbonyl)-4,5-diphenyl-1-methylimidazole, (3) N-(morpholin-4-yl)-4,5-diphenyl-1-methylimidazole-2-carboxamide,
(4) N-(piperidin-1-yl)-4,5-di-(4-methylphenyl)-1-methylimidazole-2-carboxamide,
(5) 2-(piperidin-1-ylcarbonyl)-4,5-di-(4-methylphenyl)-1-methylimidazole,
(6) N-(morpholin-4-yl)-4,5-di-(4-methylphenyl)-1-methylimidazole-2-carboxamide,
(7) 2-(pyrrolidin-1-ylcarbonyl)-4,5-di-(4-methylphenyl)-1-methylimidazole,
(8) N-(piperidin-1-yl)-4,5-di-(4-chlorophenyl)-1-methylimidazole-2-carboxamide,
(9) 2-(piperidin-1-ylcarbonyl)-4,5-di-(4-chlorophenyl)-1-methylimidazole, N-(morpholin-1-yl)-4,5-di-(4-chlorophenyl)-1-methylimidazole-2-carboxamide,
(11) N-(piperidin-1-yl)-4,5-di-(4-chlorophenyl)imidazole-2-carboxamide, N-(piperidin-1-yl)-4,5-di-(2,4-dichlorophenyl)-1-methylimidazole-2-carboxamide,
(13) N-(piperidin-1-yl)-4-(4-chlorophenyl)-5-(2,4-dichlorophenyl)-1-methylimidazole-2-carboxamide,
(14) N-(piperidin-1-yl)-4-(2,4-dichlorophenyl)-5-(4-chlorophenyl)-1-methylimidazole-2-carboxamide,
(15) N-(morpholin-4-yl)-4-(2,4-dichlorophenyl)-5-(4-chlorophenyl)-1-methylimidazole-2-carboxamide,
(16) N-(piperidin-1-yl)-4-(4-chlorophenyl)-5-(2,4-dichlorophenyl)-1-ethylimidazole-2-carboxamide,
(17) N-(piperidin-1-yl)-5-(4-chlorophenyl)-4-(2,4-dichlorophenyl)-1-methyl-imidazole-2-carboxamide,
(18) N-(pyrrolidin-1-yl)-5-(4-chlorophenyl)-4-(2,4-dichlorophenyl)-1-methyl-imidazole-2-carboxamide,
(19) N-(azepin-1-yl)-5-(4-chlorophenyl)-4-(2,4-dichlorophenyl)-1-methyl-imidazole-2-carboxamide,
(20) N-(tetrahydropyran-4-yl)-4-(2,4-dichlorophenyl)-5-(4-chlorophenyl)-1-methylimidazole-2-carboxamide,
(21) N-(2,2-dimethyl-tetrahydropyran-4-yl)-4-(2,4-dichlorophenyl)-5-(4-chlorophenyl)-1-methylimidazole-2-carboxamide,
(22) N-(piperidin-1-yl)-5-(4-chlorophenyl)-4-(2,4-dichlorophenyl)-1-ethyl-imidazole-2-carboxamide,
(23) N-(piperidin-1-yl)-5-(4-chlorophenyl)-4-(2,4-dichlorophenyl)-1-(1-methyl)ethyl-imidazole-2-carboxamide,
(24) N-(piperidin-1-yl)-5-(4-chlorophenyl)-4-(2,4-dichlorophenyl)-1-(1,1-dimethyl)ethyl-imidazole-2-carboxamide,
(25) N-(piperidin-1-yl)-5-(4-chlorophenyl)-4-(2,4-dichlorophenyl)-1-(2-dimethylamino)ethyl-imidazole-2-carboxamide,
(26) N-(piperidin-1-yl)-5-(4-chlorophenyl)-4-(2,4-dichlorophenyl)-1-propyl-imidazole-2-carboxamide,
(27) N-(piperidin-1-yl)-5-(4-chlorophenyl)-4-(2,4-dichlorophenyl)-1-butyl-imidazole-2-carboxamide,
(28) N-(piperidin-1-yl)-5-(4-chlorophenyl)-4-(2,4-dichlorophenyl)-1-(2-methoxy)ethyl-imidazole-2-carboxamide, and
(29) N-(piperidin-1-yl)-4-(2-chlorophenyl)-5-(4-chlorophenyl)-1-methyl-imidazole-2-carboxamide, and pharmaceutically acceptable salts thereof.

5. The compound according to claim 4 selected from:
(1) N-(piperidin-1-yl)-4,5-diphenyl-1-methylimidazole-2-carboxamide,
(2) 2-(piperidin-1-ylcarbonyl)-4,5-diphenyl-1-methylimidazole,
(3) N-(morpholin-4-yl)-4,5-diphenyl-1-methylimidazole-2-carboxamide,
(4) N-(piperidin-1-yl)-4,5-di-(4-methylphenyl)-1-methylimidazole-2-carboxamide,
(5) 2-(piperidin-1-ylcarbonyl)-4,5-di-(4-methylphenyl)-1-methylimidazole,
(6) N-(morpholin-4-yl)-4,5-di-(4-methylphenyl)-1-methylimidazole-2-carboxamide,
(7) 2-(pyrrolidin-1-ylcarbonyl)-4,5-di-(4-methylphenyl)-1-methylimidazole,
(8) N-(piperidin-1-yl)-4,5-di-(4-chlorophenyl)-1-methylimidazole-2-carboxamide,
(9) 2-(piperidin-1-ylcarbonyl)-4,5-di-(4-chlorophenyl)-1-methylimidazole, N-(morpholin-1-yl)-4,5-di-(4-chlorophenyl)-1-methylimidazole-2-carboxamide, N-(piperidin-1-yl)-4,5-di-(4-chlorophenyl)imidazole-2-carboxamide, N-(piperidin-1-yl)-4,5-di-2,4-dichlorophenyl)-1-methylimidazole-2-carboxamide,
(13) N-(piperidin-1-yl)-4-(4-chlorophenyl)-5-(2,4-dichlorophenyl)-1-methylimidazole-2-carboxamide,
(14) N-(piperidin-1-yl)-4-(2,4-dichlorophenyl)-5-(4-chlorophenyl)-1-methylimidazole-2-carboxamide,
(15) N-(morpholin-4-yl)-4-(2,4-dichlorophenyl)-5-(4-chlorophenyl)-1-methylimidazole-2-carboxamide, and
(16) N-(piperidin-1-yl)-4-(4-chlorophenyl)-5-(2,4-dichlorophenyl)-1-ethylimidazole-2-carboxamide,
and pharmaceutically acceptable salts thereof.

6. The compound according to claim 5, selected from:
(1) N-(piperidin-1-yl)-4-(2,4-dichlorophenyl)-5-(4-chlorophenyl)-1-methylimidazole-2-carboxamide, and
(2) N-(piperidin-1-yl)-4,5-di-(2,4-dichlorophenyl)-1-methylimidazole-2-carboxamide,
and pharmaceutically acceptable salts thereof.

7. The compound according to claim 3, wherein the compound is N-(piperidin-1-yl)-4-(2,4-dichlorophenyl)-5-(4-chlorophenyl)-1-methylimidazole-2-carboxamide, or a pharmaceutically acceptable salt thereof.

8. A composition comprising a therapeutically effective amount of a compound according to claim 3 and a pharmaceutically acceptable carrier.

* * * * *